United States Patent [19]

Mukkala et al.

[11] Patent Number: 5,216,134
[45] Date of Patent: Jun. 1, 1993

[54] SPECTROFLUOROMETRIC METHOD AND COMPOUNDS THAT ARE OF VALUE FOR THE METHOD

[75] Inventors: Veli-Matti Mukkala; Christian Sund, both of Turku; Marek Kwiatkowski, Uppsala, Sweden

[73] Assignee: Wallac Oy, Turku, Finland

[21] Appl. No.: 665,279

[22] Filed: Mar. 6, 1991

Related U.S. Application Data

[63] Continuation of Ser. No. 424,269, Oct. 23, 1989, abandoned.

[51] Int. Cl.$^5$ .................. C07F 5/00; C07D 279/00; C07K 3/00; G01N 33/533
[52] U.S. Cl. .......................... 534/15; 534/16; 530/391.3; 544/4; 546/2; 546/5; 546/6; 436/546
[58] Field of Search .......... 546/257, 258, 2, 5, 546/6; 544/4; 530/391.3; 436/546; 534/15, 16

[56] References Cited

U.S. PATENT DOCUMENTS

| | | | |
|---|---|---|---|
| 4,698,091 | 10/1987 | Brunner et al. | 71/87 |
| 4,772,563 | 9/1988 | Evangelista et al. | 436/518 |
| 4,927,923 | 5/1990 | Mathis et al. | 540/436 |

OTHER PUBLICATIONS

Kunjian Gu, Tetrahedron Letters 30 (11) pp. 1323-1326 (1989).
Alpha et al., Helv. Chim. Acta 71 (1988) pp. 1042-1052.
Newkome et al., Inorg. Chem. 23 (1984) pp. 2400-2408.
Ohm et al., Chem. Berichte 118 (1985) pp. 22-27 Melby et al., JACS 86 (1964) pp. 5117-5125.

Primary Examiner—Nicholas S. Rizzo
Assistant Examiner—Matthew V. Grumbling
Attorney, Agent, or Firm—Fred Philpitt

[57] ABSTRACT

A chelate formed between $Eu^{3+}$, $Tb^{3+}$, $Dy^{3+}$ and $Sm^{3+}$ and a compound having the formula

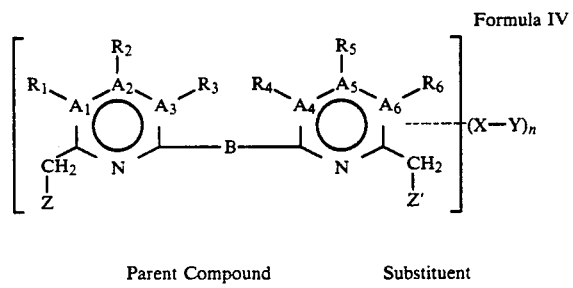

Parent Compound    Substituent where $A_{1-6}$ are single carbon or nitrogen atoms; $n=1$ or 2; $R_{1-6}$ is nothing when A is a nitrogen, and hydrogen or an organic group when A is a carbon; Z and Z' are selected among $-N(CH_2CH_2COO^-)_2$, $-N(CH_2COO^-)_2$, $-N(CH_2OPO_3^{2-})_2$ and $-N(CH_2PO_3^{2-})_2$;—species that —X—Y is a substituent replacing a hydrogen anywhere in the parent compound; and —X—Y represents an organic group containing no chelating heteroatom closer than four atoms from a chelating heteroatom in the parent compound and X is a stable bridge containing certain groups and Y is selected from (a) specified relative groups allowing coupling to other compounds and (b) residues of compounds participating in biospecific affinity reactions.

11 Claims, No Drawings

SPECTROFLUOROMETRIC METHOD AND COMPOUNDS THAT ARE OF VALUE FOR THE METHOD

This is a continuation of application Ser. No. 424,269, filed Oct. 23, 1989 now abandoned and the benefits of 35 USC 120 are claimed relative to it.

FIELD OF THE INVENTION

This invention presents a new spectrofluorometric method utilizing two or more fluorescent probes for the detection of structures (target structures) that can be specifically marked by the probes. The method falls under the wellknown concept of multiple labeling. The invention also provides new compounds that can be used either directly as probes in spectrofluorometric methods or as intermediates for the synthesis of the probes. The compounds may also have other uses. The novel compounds comprise chelating structures or ester, salt and chelate forms thereof in which one or more of the chelating heteroatoms have been transformed to said forms.

Time-resolved fluorometry is a fluorescence technique in which the lifetime of the emission occurring after a pulsed light excitation is monitored at a certain wavelength. In order to be able to utilize the benefits of time-resolved fluorescence, the labels should be fluorophores with a fluorescence lifetime considerably longer than that of the components giving rise to the background signal. The fluorescent half life of certain lanthanide chelates, such as europium, is 5-6 orders of magnitude longer than that of conventional fluorescent labels. The decay time and intensity of lanthanide fluorescence are very much dependent on the structure of the ligands which chelate the metal and on the physical environment around it. Lanthanide chelates have already found wide application in a variety of biological assays. In the only commercial methods so far, however, a two-stage procedure for developing the fluorescent signal is used. These methods comprise a biospecific affinity reaction of a reactant labeled with lanthanide chelates, followed by the release of the metal ion and formation of a new strongly fluorescent chelate (Dakubu et al., Clin. Biochem.Anal. 14, 71-101 (1984) and Lövgren et al., In: Alternative Immunoassays, Ed: Collins, W. P., John Wiley & Sons Ltd. (1985) 203-17). This can be explained by the difficulties to combine good absorption and energy transfer properties, strong chelating capacity and ability to form strong covalent bonds with labeled molecules to the same ligand.

Most of the now existing immunological or hybridization assays utilize reactions on solid supports but for technical purposes it is preferably to detect the fluorescence in homogeneous solutions. Therefore since fluorescent markers thus have to be released anyway from the solid matrix the aforesaid two-step system could find extensive application. Fluorescent lanthanide chelates have been recognized as being very promising labels. Used as markers in immunoassays they could be detected with a sensitivity at least at the same level as is commonly shown for $^{125}I$. This could, if properly realized, open up the possibility of utilizing them as markers in areas which until now have used traditional fluorescent labels. Possible candidates for such fields of application are:

1) Homogeneous fluorometric immunoassays
2) Nucleic acid sequencing
3) Fluorescence microscopy
4) Homogeneous hybridization assays for nucleic acid detection
5) Cytometry
6) Nucleic acid and protein finger printing Fluorescent chelates described heretofore, being composed of chemically different ligands, differ inter se in many aspects, but in most cases their fluorescence decay time is long enough to permit their use in time-resolved fluorescence assays. While it is commonly recognized that a high stability constant and intensive fluorescence i.e. high quantum yield, are desirable for a fluorescent chelate, some other often-discussed properties are still a matter of controversy. One of them is the dependence of the emitted light on the environment that surrounds the label. In our opinion this should be seen not as a negative, nonpredictable effect but as a new property making it possible to use fluorescent chelates in new areas, e.g. in the field of various kinds of homogeneous assays. It is apparent from the literature that most of the efforts have been focused on the development of more highly fluorescent and more stable chelates. When aspects of excitation versus emission of certain chelates were investigated, the only object of interest was to develop a chelate with a relatively long wavelength excitation maximum while at the same time preserving the large Stokes shift typical of rare earth metals. To our knowledge there are no reports on systematic studies aiming at the development of a group of chelates differing substantially in their fluorescent properties by different excitation or emission spectra, yet being derivatives of one and the same metal. This would give the possibility of using such chelates simultaneously as multiple labels in the same experiment, provided that the shapes of the excitation spectra would not substantially coincide with each other. The multiple labeling technique using traditional organic fluorescent markers is a well established method. A commonly accepted disadvantage is the comparatively fast rate of fluorescence decay of the labels employed, thus creating substantial background problems. It has been shown earlier that the use of long decay time fluorescent chelates of certain rare earth metals may drastically diminish this problem simply by permitting effective measurement of the marker fluorescence after the background signal has decayed. For some experiments, when separation of labeled components is necessary or preferred prior to their determination, and multiple labeling of all the components is the method of choice, it is advantageous to use labels with a minimal degree of difference in their physicochemical properties. For example, this requirement—not always easy to fulfill—was the main difficulty in the nonisotopic approach to nucleic acid sequencing (Smith et al. 1986, Nature pp. 674-679). Obviously there is a need for a family of fluorescent markers that do not substantially differ with regard to their chemical structure, yet exhibiting a wide spectrum of excitation or/and emission wavelengths. Another aspect of the problem, often not emphasized enough, is the dependence of the emitted fluorescent light on the type of the functional, reactive group connected to the fluorophore in order to allow its coupling to biological materials. It has been shown earlier (EP-A-171,978) that the introduction of one nitro group to the side phenyl ring system in the europium chelate of 4,7-diphenyl-1,10-phenanthroline-2,9-dicarboxylic acid diminishes the fluorescence by 60%. The reduction of this nitro group, which results in the introduction of an amino group sharing its electrons through π-type bonds with the rest of the chelate, is combined with an even greater decrease of fluorescence—in fact only 0.27% of the fluorescence of the unsubstituted compound is preserved. Recently another type of fluorescent chelates has been published (EP-A-195,413) where the substituted 4-phenyl pyridine was used as a chromophore. Since superiority of these compounds was claimed over all other fluorescent chelates and no fluorescent data was presented, we decided to check their value in practice. The compounds of the following structures have been synthesized

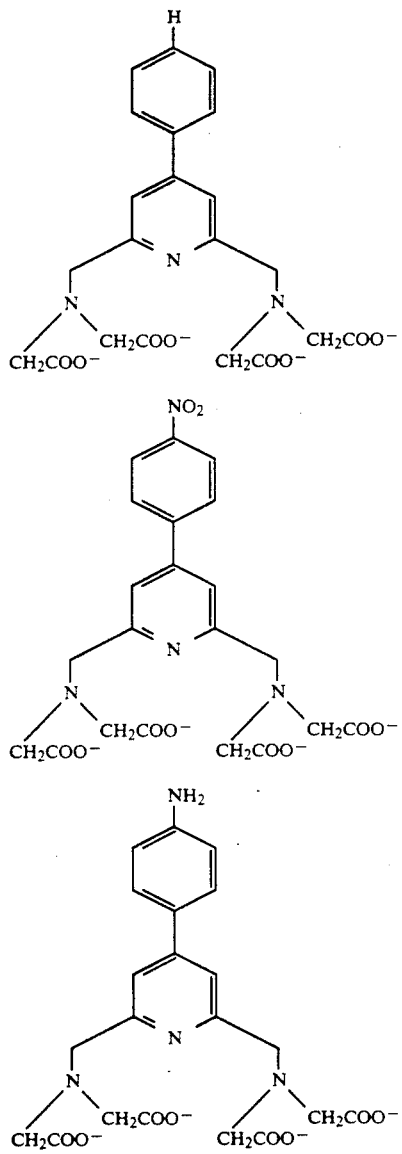

and their fluorescent properties have been measured. We found again the same tendency toward decreasing intensity of fluorescent light as the ground structure (I) is converted to (II) and (III). In particular, compound (II) in the form of the $Eu^{3+}$ chelate exhibits 8% of (I) fluorescence and compound (III) only 1.8%. Even greater differences were noted for appropriate $Tb^{3+}$ chelates. In this case the chelated compound (II) shows only 0.006% fluorescence as compared to the fluorescence of the terbium chelate of (I). It is therefore clear that a successfully employed reactive group should, if possible, always be attached in a position separating it from the chromophore in such a way that its electronic interaction with the rest of the molecule can be neglected—preferably through an aliphatic carbon chain. If this is done correctly it will also ensure that the fluorescent properties observed in simple nonreactive chelates (without any additional reactive group) will remain essentially the same if such a reactive group is connected to the chelate or if a thusfunctionalized chelate combines with biological material. Several aromatic structures have been proposed to function as light absorbing units-chromophores. Phenanthrolines have been suggested as already mentioned (EP-A-171,978). Phenanthrolines, being a chromophoric part of cryptates, are also presented in FR-A-2,570,703. Other chromophoric units have also been suggested, such as: functionalized pyridines (EP-A-195,413, EP-203,047), substituted phenols (EP-A-68,875), unsubstituted terpyridines (J. Am. Chem. Soc. 86 (23), 5117-5125, 1964), indole- and benzyl-EDTA (Photochemistry and Photobiology 39 (6), 763-769, 1984) and p-amino salicylic acid (Analyst 109, 1449-1450, 1984). Bipyridine is known to be an excellent chromophore but also a very poor chelator in itself. Attempts have been made to introduce one or more bipyridines into a cryptate chelating system (FR-A-2,570,703) as well as into other chelating systems (WO-A-87/04523).

Closely related to the present invention is the description of acidic complexone which is a derivative of bipyridine, see Chem. Berichte 118, 22-27, 1985. This paper describes however only the simplest ligand in bipyridine series, and no fluorescent rare earth metal chelate. In addition, the paper does not suggest any possibility of attaching such ligands to any other molecule.

DESCRIPTION OF THE INVENTION

One major aspect of the invention is an improved multiple labeling method for spectrofluorometric assays for the presence of specific chemical structures in a sample. The characteristic feature of this aspect of the invention is to simultaneously use at least two fluorescent lanthanide chelates as probes. The probes employed differ with respect to their excitation and/or emission wave length maxima so that they can be measured independently. Chelates having different ligands will differ in excitation wave lengths, and chelates having different rare earth metals will differ in emission wave lengths. The chelated lanthanide is $Eu^{3+}$, $Tb^{3+}$, $Sm^{3+}$ or $Dy^{3+}$. This aspect of the invention may be applied to the same general type of spectrofluorometric techniques as set forth on page 2 that utilize a single probe. Heterogeneous hybridization assays and heterogeneous immunoassays are also included. Some of the methods require removal of probe excess, but others do not (e.g. the homogeneous methods). Generally the applicable assays comprise two steps, namely (i) marking the target structure by fluorescent probes, binding specifically to said structure and (ii) measuring the fluorescence from probes. The fluorescent pattern detected will be associated with the presence of the target structure. The sequence of the two steps may be interrupted by other steps such as separation steps and/or addition of further reactants as in the case of immunoassays of various types.

The compounds of the invention have the common structure given in formula (IV) and comprise also ordinary analogs thereof, such as acid, ester, salt and chelate forms involving one or more of the chelating heteroatoms.

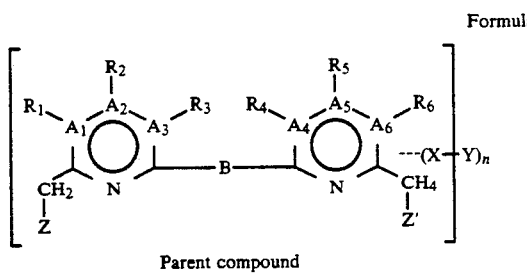

Formula IV

Parent compound

Among the compounds of the invention it is possible to select several pairs of appropriate rare earth metal chelates which will differ enough with regard to their excitation spectra to enable one of them to be selectively excited in the presence of the other. Most of the compounds described have shown a relatively high fluorescence, comparable to those fluorescent chelates which have already been described and used in different applications. Moreover, all the described chelates, being derivatives of bipyridine, bipyrimidine or closely related systems, differ very little as regards their biophysical properties such as molecular weight, hydrophobicity or electrophoretical mobility, which is of crucial importance when they are employed in experiments which involve multiple labeling.

The invention provides methods for attaching a reactive function to such chelates, a feature necessary for their coupling to a variety of biologically active molecules. Moreover, this reactive function is connected to the chelate in such a way that the fluorescence of the chelate is not changed either in the active form before coupling or after its coupling to a biological molecule. We accomplished this by introducing the reactive group into the chelating chromophoric part of the molecule via a aliphatic chain separating the two functions from each other, or via a linker system composed of both aliphatic and aromatic parts. This solution was the only acceptable one if the electronic status of the pyridine or bipyrimidine moiety was to be kept intact, in view of the very considerable changes that may be caused by substituents connected to the light absorbing aromatic system. Also, the feature that the chelating part fluorescence is independent of the presence of the attached reactive moiety has an additional advantage, namely it makes the usefulness of a given chelate as a marker potentially predictable purely on the basis of the physicochemical properties of its basic structure (chelate without a functional reactive group):

In formula (IV), n is an integer 0, 1, or 2, preferably 1, and—specifies that the group X-Y is a substituent replacing a hydrogen anywhere in the parent compound (including also e.g. cases where X-Y is a substituent on or replacing any of $R_1 R_2, R_3, R_4, R_5, R_6$). When n is 0 the compound of our invention is the parent compound in formula (IV).

B is a bridge allowing i) electron delocalization between the heterocyclic rings, and ii) simultaneous coordination of the two shown ring nitrogens with a chelated metal ion so as to form a five- or six-membered ring. Examples of bridging groups fulfilling these criteria are a direct link, —O—, —NH— or —CO—. With respect to our experimental data a direct link and —CO— are to be preferred.

$A_1$, $A_2$, $A_3$, $A_4$, $A_5$ and $A_6$ may all be carbon atoms which for our preferred compounds result in 2,2'-bipyridine or 2,2'-ketobipyridine structures. $A_1$, $A_2$, $A_3$, $A_4$, $A_5$ and $A_6$ may also denote single nitrogen atoms. In the preferred embodiment only one in the group $A_1$, $A_2$, $A_3$ and/or only one in the group $A_4$, $A_5$, $A_6$ is a nitrogen atom e.g. $A_1$ or $A_3$ and/or $A_4$ or $A_6$. For the case of B being a direct link this corresponds to the structure of 2-pyridino-2'-pyrimidines or 2,2'-bipyrimidines or the corresponding bipyridazine compounds. The 2,2'-bipyrimidines are usually symmetric but the synthetic methods employed by us do not exclude unsymmetrical bipyrimidines either. The mentioned nitrogen atoms may exist free or may be oxidized to form N-oxides.

Each of $R_1$-$R_6$ is nothing when the A to which it is attached is a nitrogen, and for each A that is a carbon $R_1$-$R_6$ are selected among:

a) hydrogen b) hydrocarbon group which may be straight, branched or cyclic, such as alkyl, alkenyl, alkynyl and an aromatic group (aryl), and optionally containing additional structures not participating in the chelation like aromatic ring systems, ether, thioether, ester, amido, amino (primary, secondary or tertiary), carboxy, halo, cyano etc., and other structures exhibiting heteroatoms, c) cyano, halo and nitro, and d) carboxylic acid (COOH), amido (CONH$_2$), amino (NH$_2$), hydroxy (OH) and substituted forms of these four groups in which a hydrogen has been replaced with a hydrocarbon group according to point b) above, and in case of the amino and hydroxy groups the hydrogens also have the possibility of being replaced with an acyl group, RCO, in which R is an hydrocarbon group according to point b) above.

Examples of alkyl are lower alkyls having less than 12 carbon atoms.

Examples of aromatic groups are phenyl, quinolyl, naphthyl, pyridyl, pyrimidyl etc. all of which may contain additional substituents. By selecting alkenyl, alkynyl or an aromatic system directly bound or bound via a carbonyl or a nitrogen atom to either one of the two heteroaromatic rings in formula (IV), the conjugated electron system can be extended to three, four or more aromatic rings or carbon atoms.

The nitrogen at any position in the central aromatic system may also exist in oxidized form, e.g. N-oxide.

Z and Z' represent identical or different chelating structures, each of which comprises at least one, preferably more than two or three, heteroatoms having a free pair of electrons and so positioned that the heteroatoms together with the nitrogen atoms of the heteroaromatic rings shown are capable of chelating a metal ion. Examples of efficient chelating heteroatoms are amino nitrogen atoms (primary, secondary and tertiary amines), negatively charged oxygen atoms, e.g. in carboxylate anions (COO$^-$), enolate anions (C=C—O$^-$) phosphates or phosphonates. Another good chelating structure is the hydroxamate group (CONOH). Efficient chelating also puts certain steric requirements on the bridge linking two chelating heteroatoms together. These heteroatoms should be placed at a distance of two atoms from each other, but three atoms distance may be acceptable. In most cases the bridge contains 1, 2 or 3 aliphatic carbon atoms. Among particularly important Z and Z' structures may be mentioned N-biscarboxymethyl and N-biscarboxyethyl amino groups and the analogous phosphate ($-N(-CH_2-O-PO_3^{2-})_2$) and phosphonate ($-N(-CH_2-PO_3^{2-})_2$). The chelating heteroatoms (N and O) may exist as the corresponding protonated forms and in the case of O also as ester forms such as lower alkyl ($C_1$-$C_6$) or benzyl esters. In view of spectrofluorometric considerations Z and Z' are preferably chelated to $Eu^{3+}$, $Tb^{3+}$, $Dy^{3+}$ or $Sm^{3+}$.

X-Y represents an inert organic group in which X is an inert and stable bridge and Y is (a) a functional group or (b) a residue of an organic compound (Y') that has properties retained in the compound of formula (IV) ($n \neq 1$ or 2) after is has been coupled covalently to the parent compound. The term "inert" above means that the group or bridge characterized by this adjective does not have any efficient chelating heteroatom closer at on a distance of four atoms from the heteroatoms participating in the chelation of a metal ion. In actual practice this means that the four atoms are normally represented by a four carbon chain. The term "stable" means that the bridge X does not deteriorate when the compounds of the invention are used, for instance the bridge does not easily undergo hydrolysis. In formula (IV), X-Y exists preferably as a substituent replacing a hydrogen in the Z and/or Z' groups, for instance in an N-biscarboxymethyl group. X-Y may also exist as a substituent on or replacing any of $R_1$, $R_2$, $R_3$, $R_4$, $R_5$ and $R_6$, and then preferably one of the Rs is replaced with X-Y.

In addition to the requirement that the bridge X must have an aliphatic carbon, preferably a methylene group ($-CH_2-$), in the bridging chain when attached directly to a heterocyclic ring of formula (IV), X may also contain at least one structural element selected from among the following: —NR— (secondary and tertiary amine), —CONR— and —NRCO— (substituted amide), —S—S— (aliphatic disulfide), —S— (aliphatic thioether), —O— (ether), —COO— and —OOC— (ester), —N=N— (diaza) and pure hydrocarbon chain which may be straight, branched or cyclic and contain from 1 to 12 carbon atoms. The carbon chain may be purely aliphatic or purely aromatic (including phenyl, naphthyl, quinolyl, pyridyl and bipyridyl), but it may also exhibit both types of structures, such as in alkylaryl, and other inert functional groups not participating in the chelation mentioned above. The symbol R in the substituted amide above represents preferably hydrogen but may be alkyl, for instance an alkyl having less than 5 carbon atoms. The same applies to R in —NR—.

Y may be selected from two main categories (A and B below):

A) Y may be the residue of an organic compound (Y') having certain properties which are substantially retained in the compound of formula (IV) (n=0). The compound (Y') may be a biologically active molecule having the ability to participate in biospecific affinity reactions, such as between antigens (haptens) and the homologous antibody active components, complementary nucleic acids (RNA, DNA), lectins and carbohydrate structures, protein A and IgG etc. These types of biologically active molecules are often called targeting substances (targeting molecules). Usually they have been or can easily be derivatized to contain functional groups permitting conjugation to diversified types of compounds. The compound (Y') may also be a multifunctional organic compound which is bound by one of its functional groups to the bridge X so as to leave at least one of its remaining functional groups free for further derivatization.

B) Y may be a functional group so selected that it can be made to react chemically with a functional group A of an organic compound (Y') so as to form a covalent linkage between Y' and a compound of formula (IV). The selection of Y depends on A and vice versa, but it is believed that any artisan can make the proper selection of mutually reactive groups. Y and A may be selected from among electrophilic and nucleophilic groups. If they are a pair of electrophilic groups or a pair of nucleophilic groups, it is possible for instance to (a) employ oxidative coupling for forming the bond (e.g. $-SH + HS- \rightarrow -S-S-$) or (b) convert one of the groups of the pair chemically to a group of the opposite type. An example of the latter case is the activation with bifunctional coupling reagents (also called activation reagents). If Y is nucleophilic and A electrophilic or vice versa these two groups can usually be reacted with each other without any preceding activation. Most nucleophilic groups comprise a heteroatom having an electron pair available for reaction with an electron deficient atom (electrophilic group).

Examples of suitable functional groups include isothiocyanato, bromoacetamido, iodoacetamido, succinamido, pyridyldithio, mercapto, carboxyl and its active esters (e.g. N-hydroxysuccinimido or p-nitrophenyl), hydroxyl, aldehyde, amino, diazonium, tosyl, mesytylyl, trexyl, phosphodiester or phosphotriester. Other functional groups are known to those skilled in the art.

In a compound according to the invention it is imperative that all the groups mentioned can coexist. However, the reactive group Y does not necessarily have to coexist with a chelate form of the invention. For some purposes the chelating part of the molecule may be temporarily protected e.g. in the form of an ester so that the protected ligand will be coupled to the target molecule, and after deblocking may finally form the desired labeled product. The protective group is chosen in accordance with known principles (see for instance Protective Groups in Organic Synthesis; Greene Tenn.; John Wiley & Sons Inc; USA (1981)). Factors to be taken into account when the group is chosen are inter alia the stability of the compound with which Y is to be reacted, the reactivity of Y and the type of structure formed upon reaction of Y and the compound intended.

One aspect of the invention comprises the use of a compound of formula (IV) ($n \neq 0$) for binding the fluorescent structure of the parent compound covalently to an organic compound (Y') having at least one functional group A which is reactive with Y. After the covalent binding reaction, and if an acid, ester or salt form as defined above has been used, the product is converted in a manner known per se to the appropriate chelate. The reaction conditions for the binding depend on the pair of functional groups (Y) and (A), Y' and the compound of formula (IV) used etc. and are known per se. In this aspect of the invention $A_1$-$A_6$, $R_1$-$R_6$, Z, Z', X, Y, n and — have the aforesaid meanings except that Y can only be a functional group and $n \neq 0$.

Protective groups known per se are sometimes required in order to perform the binding. See the above-mentioned text-book.

The invention is defined in the appended claims which are part of the description.

The invention will now be illustrated by way of the synthesis and use of a large number of compounds. Their structure as well as the synthetic routes for their preparation are shown on separate formula pages (53–64). In case of discrepancies between a given name and the corresponding structural formula, the latter has precedence.

EXAMPLE 1

Scheme 1, x=y=H 6,6'-Dimethyl-2,2'-bipyridine (1)

Ref. G. R. Newkome et al., J. Inorg. Nucl. Chem., 43, 1529-1531 (1981)

6-Bromo-2-methylpyridine (49.0 g, 0.285 moles), benzyltriethylammonium chloride (11.6 g, 0.0509 moles), sodium formate (25.7 g, 0.408 moles), 10% palladium on carbon (1.7 g), 32% sodium hydroxide (29 ml) and water (86 ml) were refluxed for 24 hours. The mixture was filtered and the aqueous phase was extracted with methylene chloride. After evaporation of solvent the product was distilled.

Yield: 59% m.p. 82°–83° C. (Lit. 88°–89° C.)

UV (in ethanol): 290 nm, 237 nm $^1$HNMR (400 MHz, CDCl$_3$): 2.61 (s, 6H); 7.11 (d, 2H, J=7.6 Hz); 7.64 (t, 2H, 7.6 Hz); 8.18 (d, 2H, J=7.6 Hz)

EXAMPLE 2

Scheme 2

2-Bromo-4-methylpyrimidine (2)

Ref. D. D. Bly et al., J. Org. Chem., 27, 2945-(1962)

To the mixture containing 2-amino-4-methylpyrimidine (40.0 g, 0.367 moles), sodium bromide (180 g, 1.75 moles), sodium nitrite (60.0 g, 0.870 moles) and water (160 ml), 100 ml of concentrated hydrobromic acid was added slowly. The temperature was kept below 0° C. during the addition. After stirring for four hours at −5° C.–+5° C. the temperature was raised to room temperature and the mixture was neutralized with concentrated sodium hydroxide solution. The product was extracted from the aqueous phase with chloroform. After evaporation of the solvent the product was distilled in vacuum.

Yield: 23% b.p. 69°–70° C./0.6 mm

UV (in ethanol): 255 nm $^1$HNMR (60 MHz, CDCl$_3$): 2.54 (s, 3H); 7.17 (d, 1H, J=5 Hz); 8.42 (d, 1H, 5 Hz)

EXAMPLE 3

Scheme 2

4,4'-Dimethyl-2,2'-bipyrimidine (3)

According to: M. Tiecco et al., Synthesis 736 (1984)

Nickel chloride hexahydrate (8.48 g, 35.7 mmoles) and triphenylphosphine (37.4 g, 143 mmoles) were dissolved in 180 ml dimethylformamide at 50° C. After bubbling nitrogen through the solution for 20 min 2.30 grams (0.0352 gr.-atoms) zinc powder was added and the mixture was stirred for one hour. 2-Bromo-4-methylpyrimidine (2) (6.25 g, 36.1 mmoles) was added and the mixture was kept at 50° C. for 3.5 hours. After pouring the mixture into 500 ml of diluted ammonia solution the organic material was extracted with chloroform. The product was extracted from chloroform with 1-N hydrochloric acid. The hydrochloric acid solution was made alkaline and extracted with chloroform. The solvent was evaporated and the product was purified by means of flash chromatography.

Yield: 12%

UV (in ethanol): 248 nm $^1$HNMR (60 MHz, CDCl$_3$): 2.72 (s, 6H); 7.28 (d, 2H, J=5 Hz); 8.86 (d, 2H, J=5 Hz)

EXAMPLE 4

5-Bromo-6,6'-dimethyl-2,2'-bipyridine (4)

According to: G. R. Newkome et al., J. Inorg. Nucl. Chem. 43, 1529 (1981)

2,5-Dibromo-6-methylpyridine (1.25 g, 5.0 mmoles), sodium formate (0.51 g, 7.5 mmoles), 10% palladium on carbon (30 mg), benzyltriethylammonium chloride (0.20 g, 0.88 mmoles) and 8% sodium hydroxide solution (2.0 ml) were refluxed for two days. The mixture was filtered and the aqueous phase was extracted with methylene chloride. The organic phase was dried, the solvent was evaporated and the product was purified by means of flash chromatography (silica, methylene chloride). The main product was a monobromo substituted compound.

Yield: 35%

UV (in ethanol): 296 nm, 251 nm, 245 nm $^1$HNMR (400 MHz, CDCl$_3$): 2.61 (s, 3H); 2.73 (s, 3H); 7.16 (d, 1H, J=7.6 Hz); 7.67 (t, 1H, 7.6 Hz); 7.88 (d, 1H, J=8.5 Hz); 8.12 (d, 1H, J=8.5 Hz); 8.19 (d, 1H, J=7.6 Hz)

EXAMPLE 5

Scheme 3

3,3'-Dihydroxy-6,6'-dimethyl-2,2'-bipyridine (5)

Ref. J. Rebek et al., J. Heterocycl. Chem., 17, 749-751 (1980)

6-Methyl-3-hydroxypyridine (23.9 g, 0.219 moles), lead dioxide (98.3 g, 0.411 moles) and toluene (1 liter) were combined and refluxed for five hours. The hot solution was filtered and evaporated to dryness. The residue was refluxed with hexane and filtered while hot. The solution was evaporated to dryness giving the product as a yellow powder.

Yield: 9.3%

UV (in ethanol): 350 nm, 246 nm $^1$HNMR (400 MHz, CDCl$_3$): 2.52 (s, 6H); 7.10 (d, 2H, J=8.2 Hz); 7.31 (d, 2H, J=8.2 Hz)

EXAMPLE 6

Scheme 3

3,3'-Dibenzoyloxy-6,6'-dimethyl-2,2'-bipyridine (6)

3,3'-Dihydroxy-6,6'-dimethyl-2,2'-bipyridine (5) (0.22 g, 1.02 mmoles) was dissolved in 12 ml pyridine and benzoylchloride (0.30 g, 2.13 mmoles) was added. After stirring for 1.5 hours at room temperature, 100 ml chloroform was added and the solution was extracted with 100 ml saturated sodium hydrogen carbonate solution. The chloroform phase was dried and evaporated to dryness. The product was crystallized as a grey powder from cyclohexane.

Yield: 51%

UV (in ethanol): 276 nm, 232 nm $^1$HNMR (400 MHz, CDCl$_3$): 2.33 (s, 6H); 7.17 (d, 2H, J=9 Hz); 7.43 (t, 4H, J=8 Hz); 7.58 (t, 2H, J=8 Hz); 7.60 (d, 2H, J=9 Hz); 8.01 (d, 4H, J=8 Hz)

EXAMPLE 7

Scheme 4

3,3'-Dicarboxy-6,6'-dimethyl-2,2'-bipyridine (7)

According to: F. L. Wimmer et al., Org. Prep. Proced. 15, 368 (1983).

Neocuproin hydrochloride (2.5 g, 12.1 mmoles), sodium hydroxide (0.76 g), potassium permanganate (4.51 g) and water (60 ml) were refluxed for 24 hours. After filtration the solvent was evaporated to half volume. The pH was adjusted to 2 with concentrated hydrochloric acid and some activated charcoal was added. After 10 minutes charcoal was filtered off and the product was precipitated with ethanol. The precipitated powder was filtered and crystallized from ethanol.

Yield: 22%

UV (in ethanol): 270 nm, 226 nm $^1$HNMR (400 MHz, DMSO): 2.60 (s, 6H); 7.58 (d, 2H, J=8.1 Hz); 8.38 (d, 2H, J=8.1 Hz)

EXAMPLE 8

Scheme 4

3,3'-Bis(carbethoxy)-6,6'-dimethyl-2,2'-bipyridine (8)

Thionyl chloride (0.5 ml) was added to 10 ml of dry ethanol. After 15 minutes, 3,3'-dicarboxy-6,6'-dimethyl-2,2'-bipyridine (740 mg, 2.7 mmoles) was added and the mixture was refluxed overnight. The mixture was poured onto ice and the solution was neutralized with sodium hydrogen carbonate. The product was extracted with ethyl acetate, dried and evaporated.

Yield: 16%

UV (in ethanol): 270 nm, 227 nm $^1$HNMR (400 MHz, CDCl$_3$): 1.01 (t, 6H, J=7.0 Hz); 2.63 (s, 6H); 4.08 (q, 4H, J=7.0 Hz); 7.28 (d, 2H, J=8.1 Hz); 8.28 (d, 2H, J=8.1 Hz)

EXAMPLE 9

Scheme 5, R=C$_6$H$_5$—CH$_5$—CH=CH=styryl 5,6-Dioxo-1,10-diphenyl-deca-1,3,7,9-tetraene (9)

Ref. P. Karrer et al., Helv. Chim. Acta,, 28, 1181-1184 (1945)

A mixture of 2,3-butanedione (30.0 g, 0.348 moles), trans-cinnamaldehyde (92.0 g, 0.696 moles), ethanol (100 ml) and piperidine (2 ml) was refluxed overnight. After cooling to 0° C. the crystallized product was filtered, washed with cold ethanol and recrystallized from ethanol.

Yield: 24%

UV (in ethanol): 367 nm $^1$HNMR (400 MHz, CDCl$_3$): 6.93-7.08 (m, 6H); 7.34-7.40 (m, 6H); 7.49-7.51 (dd, 4H, J=1.5 Hz & 8.0 Hz);.7.58-7.65 (m, 2H)

EXAMPLE 10

Scheme 5

6,6'-Dimethyl-4,4'-distyryl-2,2'-bipyridine (10)

Ref. F. Kröhnke, Synthesis, 1-24 (1976)

5,6-Dioxo-1,10-diphenyldeca-1,3,7,9-tetraene (9) (15.7 g, 50 mmoles), acetonylpyridinium chloride (17.2 g, 100 mmoles), ammonium acetate (100 g) and methanol (500 ml) were refluxed for two hours. After cooling the product was filtered, washed with ethanol and crystallized from dimethyl formamide.

Yield: 14%

UV (in ethanol): 311 nm $^1$HNMR (60 MHz, CDCl$_3$): 2.68 (s, 6H); 7.20-7.61 (m, 16H); 8.34 (s, 2H)

EXAMPLE 11

Scheme 6, starting material

6-Bromo-2-dimethoxymethyl pyridine (11)

6-Bromo-2-pyridinecarboxaldehyde J. Am. Chem. Soc. 91, (11), 3500 (1970) (11.38 g, 62.2 mmoles) was dissolved in a mixture of dry methanol (200 ml) and trimethyl orthoformate (26.5 g, 250 mmoles). After addition of p-toluenesulfonic acid monohydrate (250 mg) the mixture was refluxed for 1 h, cooled and neutralized by addition of pyridine (5 ml). Evaporation of solvent and distillation of the product under reduced pressure yielded pure dimethylacetal as a colorless liquid.

Yield: 96%

$^1$HNMR (60 MHz, CDCl$_3$): 3.36 (s, 6H); 5.25 (s, 1H); 7.46 (m, 3H)

EXAMPLE 12

Scheme 6

Bis(6-dimethoxymethyl-2-pyridyl)ketone (12)

6-Bromo-2-dimethoxymethyl pyridine (11) (14.2 g, 61 mmoles) was dissolved in dry diethyl ether (200 ml) and cooled down to −70° C. in a round bottom three-necked flask equipped with reflux condenser and dropping funnel while a gentle flow of dry argon was passing through the magnetically stirred mixture. Butyllithium (25.1 ml (2.6M), 65.3 mmoles) was added dropwise and the temperature of the reaction mixture was kept below −60° C. After completion of this addition the mixture was stirred for an additional 1 h, and ethyl chloroformate (4.52 g, 41.7 mmoles) dissolved in dry diethyl ether was then introduced at a rate such that the temperature did not exceed −60° C. The yellow suspension was stirred for 45 min at −60° C. and then additionally for 15 min at −40° C. The reaction was quenched with methanol (20 ml) and the reaction mixture was poured into saturated aqueous sodium hydrogen carbonate (300 ml). The ether phase was separated and the aqueous phase was extracted twice with 100 ml of dichloromethane. The combined organic phase was evaporated and coevaporated with toluene which yielded crude title compound (12).

$^1$HNMR (60 MHz, CDCl$_3$): 3.38 (s, 12H); 5.30 (s, 2H); 8.18-7.64 (m, 6H)

EXAMPLE 13

Scheme 6

Bis(6-formyl-2-pyridyl)ketone (13)

Crude bis(6-dimethoxymethyl-2-pyridyl)ketone (12) was dissolved in dioxane (40 ml) and water (25 ml). Concentrated hydrochloric acid (3 ml) was added and the magnetically stirred mixture was boiled for 15 min. The dark solution was then poured into saturated sodium hydrogen carbonate solution (100 ml) and extracted with chloroform (3×100 ml). The residue after evaporation of the combined extracts was filtered through a short silica gel column using 4% EtOH/CHCl$_3$ as a solvent and the fractions containing the product were evaporated. The product was crystallized from hot toluene (100 ml).

Yield: 65% (based on compound 11)

$^1$HNMR (60 MHz, CDCl$_3$): 8.48–8.11 (m, 6H); 10.07 (s, 2H)

EXAMPLE 14

Scheme 6

Bis(6-hydroxymethyl-2-pyridyl)ketone (14)

To the compound (13) (2.5 g, 52.5 mmoles) in dry ethanol (50 ml) sodium borohydride (400 mg, 52.5 mmoles) dissolved in dry ethanol (30 ml) was added dropwise at 0° C. with gentle stirring. A satisfactory ratio of diol (14)/triol was obtained when about ⅔ of the borohydride had been added. Acetone (20 ml) was added for destroying unreacted reducing agent and the mixture was evaporated, dissolved in chloroform/ethanol 1:1 and extracted with saturated sodium hydrogen carbonate. The organic phase was evaporated, coevaporated with toluene and purified by silica gel column chromatography using EtOH/CHCl$_3$ 1:9 as an eluting solvent.

Yield: 48%

$^1$HNMR (60 MHz, CDCl$_3$+CD$_3$OD): 4.77 (s, 4H); 7.98–7.27 (m, 6H)

EXAMPLE 15

Scheme 8

6,6'-Dimethyl-2,2'-bipyridine-N-oxide (15)

6,6'-Dimethyl-2,2'-bipyridine (1.97 g, 0.0107 moles, Example 1) was dissolved in chloroform (10 ml). m-Chloroperbenzoic acid (1.85 g, 0.0107 moles) was dissolved in chloroform (40 ml), and added slowly to the bipyridine solution at 0°–5° C. After stirring for two hours at room temperature the solution was extracted twice with saturated sodium hydrogen carbonate solution and three times with water. The chloroform phase was dried and evaporated. The product was purified by flash chromatography.

Yield: 70%

UV (in ethanol): 270 nm, 250 nm $^1$HNMR (400 MHz, CDCl$_3$): 2.61 (s, 3H); 2.62 (s, 3H); 7.19 (d, 1H, J=8 Hz); 7.28 (d, 1H, J=5 Hz); 7.69 (t, 1H, J=8 Hz); 7.97 (t, 1H, J=5 Hz); 8.53 (d, 1H, J=8 Hz)

EXAMPLE 16

Scheme 8

6,6'-Dimethyl-2,2'-bipyridine-N,N'-dioxide (16)

6,6'-Dimethyl-2,2'-bipyridine (10.0 g, 0.054 moles) was dissolved in chloroform (50 ml). m-Chloroperbenzoic acid (21.0 g, 0.122 moles) was dissolved in chloroform (200 ml) and the solutions were combined. After stirring at room temperature overnight the solvent was evaporated and the product was purified by means of flash chromatography (silica, 0–30% methanol/chloroform).

Yield: 68%

UV (in ethanol): 263 nm, 225 nm $^1$HNMR (400 MHz, CDCl$_3$): 2.58 (s, 6H); 7.23 (t, 2H, J=8 Hz); 7.34 (dd, 2H, J=8 Hz & 2 Hz); 7.36 (dd, 2H, J=8 Hz & 2 Hz)

EXAMPLE 17

Scheme 8

6,6'-Dimethyl-4-nitro-2,2'-bipyridine-N-oxide (17)

6,6'-Dimethyl-2,2'-bipyridine-N-oxide (1.50 g, 0.00749 moles) was dissolved in concentrated sulfuric acid (8.0 ml) and fuming nitric acid (6.0 ml) and the mixture was heated at 100° C. for four hours. The solution was poured slowly into ice-water and the pH was adjusted to 5.5 with 10% sodium hydroxide. The product was filtered and dried.

Yield: 53% m.p. 160°–163° C.

UV (in ethanol): 337 nm, 294 nm, 233 nm $^1$HNMR (400 MHz, CDCl$_3$): 2.62 (s, 3H); 2.65 (s, 3H); 7.27 (d, 1H, J=8 Hz); 7.75 (t, 1H, J=8 Hz); 8.10 (d, 1H, J=3 Hz); 8.56 (d, 1H, J=8 Hz); 8.93 (d, 1H, J=3 Hz)

EXAMPLE 18

Scheme 8

6,6-Dimethyl-4,4'-dinitro-2,2'-bipyridine-N,N'-dioxide (18)

6,6'-Dimethyl-2,2'-bipyridine-N,N'-dioxide (6.84 g, 0.0316 moles) was stirred with concentrated sulfuric acid (33.5 ml) and fuming nitric acid (25.0 ml) at 100° C. for five hours. The pH was adjusted to 5.5 with 10% sodium hydroxide. The precipitated product was filtered and dried in vacuum.

Yield: 48%

UV (in ethanol): 336 nm $^1$HNMR (400 MHz, DMSO): 2.48 (s, 6H); 8.53 (d, 2H, J=4 Hz); 8.61 (d, 2H, J=4 Hz)

EXAMPLE 19

Scheme 8

4-Bromo-6,6'-dimethyl-2,2'-bipyridine (19)

6,6'-Dimethyl-4-nitro-2,2'-bipyridine-N-oxide (0.50 g, 2.0 mmoles) was dissolved in acetyl bromide (10.0 ml) and phosphorus tribromide (2.5 ml). After refluxing for 1.5 hours the mixture was poured into 100 g ice and the solution was neutralized with 30% sodium hydroxide solution. The mixture was extracted with chloroform, the chloroform phase was dried and evaporated. The product was purified by means of flash chromatography.

UV (in ethanol): 291 nm, 242 nm, 217 nm $^1$HNMR (400 MHz, CDCl$_3$): 2.59 (s, 3H); 2.62 (s, 3H); 7.17 (d, 1H, J=7.6 Hz); 7.33 (d, 1H, 1.5 Hz); 7.68 (t, 1H, J=7.6 Hz); 8.17 (d, 1H, J=7.6 Hz); 8.41 (d, 1H, J=1.5 Hz)

EXAMPLE 20

Scheme 8

4-Amino-6,6'-dimethyl-2,2'-bipyridine (20)

6,6'-Dimethyl-4-nitro-2,2'-bipyridine-N-oxide (17) (2.0 g, 8.2 mmoles) was dissolved in methanol (20 ml). 10% palladium on carbon (0.36 g) was added followed by slow addition of sodium borohydride (3.6 g, 95 mmoles). After one hour the reaction mixture was filtered and the solution was evaporated. The residue was dissolved in 0.1N sodium hydroxide solution and the product was extracted with chloroform from the water phase. The chloroform phase was dried and evaporated.

Yield: 80% m.p. 101°–103° C.

UV (in ethanol): 284 nm, 236 nm $^1$HNMR (400 MHz, CDCl$_3$): 2.48 (s, 3H); 2.61 (s, 3H); 6.40 (d, 1H, J=2.1 Hz); 7.12 (d, 1H, J=7.6 Hz); 7.47 (d, 1H, J=2.1 Hz); 7.65 (t, 1H, 7.6 Hz); 8.13 (d, 1H, J=7.6 Hz)

EXAMPLE 21

6,6'-Dimethyl-4-ethoxy-2,2'-bipyridine-N-oxide (21)

6,6'-Dimethyl-4-nitro-2,2'-bipyridine-N-oxide (17) (1.0 g, 4.1 mmoles) was added to sodium ethoxide solution made from (0.19 g, 0.0083 g-atoms) sodium and 25 ml ethanol. The mixture was stirred at 70° C. for 30 minutes. After neutralization with concentrated hydrochloric acid the reaction mixture was filtered and evaporated to dryness. The product was purified by means of flash chromatography (silica, 0%–50% methanol/chloroform).

Yield: 90%

UV (in ethanol): 272 nm, 239 nm $^1$HNMR (400 MHz, CDCl$_3$): 1.45 (t, 3H, J=7.0 Hz); 2.58 (s, 3H); 2.61 (s, 3H); 4.14 (q, 2H, J=7.0 Hz); 6.84 (d, 1H, J=3.4 Hz); 7.20 (d, 1H, J=7.7 Hz); 7.54 (d, 1H, J=3.4 Hz); 7.70 (t, 1H, 7.7 Hz); 8.65 (d, 1H, J=7.7 Hz)

EXAMPLE 22

Scheme 8

6,6'-Dimethyl-4-ethoxy-2,2'-bipyridine (22)

6,6'-Dimethyl-4-ethoxy-2,2'-bipyridine-N-oxide (21) (0.96 g, 3.93 mmoles) was dissolved in chloroform (34 ml). After addition of phosphorus tribromide (3.0 ml) the mixture was refluxed for 1.5 hours. The solution was poured on ice, some chloroform was added and the phases were separated. The chloroform phase was extracted with water. The aqueous phases were combined, made alkaline with sodium hydroxide solution, and extracted with chloroform. Evaporation of the organic phase followed by silica gel chromatography yielded pure title product. Yield: 69%

UV (in ethanol): 286 nm, 243 nm $^1$HNMR (400 MHz, CDCl$_3$): 1.45 (t, 3H, J=7.0 Hz); 2.56 (s, 3H); 2.62 (s, 3H); 4.18 (q, 2H, J=7.0 Hz); 6.67 (d, 1H, J=2.1 Hz); 7.14 (d, 1H, J=7.6 Hz); 7.67 (t, 1H, J=7.6 Hz); 7.75 (d, 1H, J=2.1 Hz); 8.16 (d, 1H, J=7.6 Hz).

EXAMPLE 23

Scheme 9

4-(2-hydroxyethoxy)-6,6'-dimethyl-2,2'-bipyridine-N-oxide (23)

Sodium hydride (2.07 g, 51.8 mmoles) was added to 1,2-dihydroxyethane (100 ml). After 15 minutes 6,6'-dimethyl-4-nitro-2,2'-bipyridine-N-oxide (17) (6.35 g, 25.9 mmoles) was added and the mixture was stirred at 60° C. for 4 hours. Excess of 1,2-dihydroxyethane was removed by evaporation in high vacuum and the product was purified by flash chromatography.

Yield: 79%

$^1$HNMR (60 MHz, CDCl$_3$): 2.52 (s, 3H); 2.57 (s, 3H); 3.83–4.06 (m, 4H); 6.80 (d, 1H, J=4 Hz); 7.16 (d, 1H, J=8 Hz); 7.45 (d, 1H, J=4 Hz); 7.66 (t, 1H, J=8 Hz); 8.27 (d, 1H, J=8 Hz)

EXAMPLE 24

Scheme 9

4-(2-hydroxyethoxy)-6,6'-dimethyl-2,2'-bipyridine (24)

4-(2-hydroxyethoxy)-6,6'-dimethyl-2,2'-bipyridine-N-oxide (23) (2.40 g, 9.22 mmoles) was dissolved in methanol (75 ml). 10% palladium on carbon (0.54 g) was added and then slowly sodium borohydride (3.24 g, 85.6 mmoles). Palladium on carbon was filtered out and the solvent was evaporated. The product was purified by means of flash chromatography (silica, 5–50% methanol/chloroform).

Yield: 91%

$^1$HNMR (60 MHz, CDCl$_3$): 2.57 (s, 3H); 2.61 (s, 3H); 3.98–4.25 (m, 4H); 6.69 (d, 1H, J=2 Hz); 7.14 (d, 1H, J=7 Hz); 7.67 (t, 1H, J=7 Hz); 7.81 (d, 1H, J=2 Hz); 8.19 (d, 1H, J=7 Hz)

EXAMPLE 25

Scheme 9

4-(2-benzoyloxyethoxy)-6,6'-dimethyl-2,2'-bipyridine (25)

4-(2-Hydroxyethoxy)-6,6'-dimethyl-2,2'-bipyridine (24) (1.0 g, 4.1 mmoles) was dissolved in dry pyridine (20 ml), and benzoyl chloride (0.63 g, 4.5 mmoles) was added. After 30 minutes chloroform (50 ml) was added and the solution was extracted with saturated sodium bicarbonate. The chloroform phase was dried and the solvent was evaporated and coevaporated with dry toluene. The product was purified by means of flash chromatography (silica, 0–50% methanol/dichloromethane).

Yield: 56% m.p. 81°–83° C.

$^1$HNMR (60 MHz, CDCl$_3$): 2.55 (s, 3H); 2.60 (s, 3H); 3.96–4.22 (m, 4H); 6.71 (d, 1H, J=2 Hz); 7.13 (d, 1H, J=8 Hz); 7.36–7.56 (m, 3H); 7.65 (t, 1H, J=8 Hz); 7.86 (d, 1H, J=2 Hz); 7.98–8.14 (m, 2H); 8.20 (d, 1H, J=8 Hz)

EXAMPLE 26

Scheme 10, starting material 4,4',6,6'-Tetramethyl-2,2'-bipyridine (26)

This compound has been synthesized in a method analogous to the one of Example 1 using 2-bromo-4,6-dimethyl pyridine as a starting material.

UV (in ethanol): 289 nm, 241 nm $^1$HNMR (400 MHz, CDCl$_3$): 2.35 (s, 6H); 2.56 (s, 6H); 6.94 (s, 2H); 8.00 (s, 2H)

EXAMPLE 27

Scheme 10

4,4'-Bis(2-phenylethyl)-6,6'-dimethyl-2,2'-bipyridine (27)

To liquid ammonia (20 ml) at −50° C. enough sodium was added to maintain a blue colored solution. Iron (III) nitrate (20 mg) was added and then sodium (0.19 g, 0.008 gr.atom). After 45 minutes 4,4',6,6'-tetramethyl-2,2'-bipyridine (26) (1.06 g, 5.00 mmoles) was added in small portions and the mixture was stirred for 1.5 hours at −50° C. Benzyl bromide (1.88 g, 11.0 mmoles) was added at −50° C. during 2 hours. The mixture was allowed to warm and water (50 ml), ethanol (20 ml) and chloroform (30 ml) was added. The organic phase was extracted with saturated ammonium sulfate solution, dried with magnesium sulfate and evaporated. By addition of ethyl acetate some pure compound was precipitated. The rest was purified by means of flash chromatography (silica, 0–6% methanol/dichloromethane).

Yield: 53%

UV (in ethanol): 290 nm, 241 nm $^1$HNMR (400 MHz, CDCl$_3$): 2.60 (s, 6H); 2.98 (bs, 8H); 6.97 (s, 2H); 7.18–7.35 (m, 10H); 8.07 (s, 2H)

EXAMPLE 28

Scheme 10

4,4'-Bis(2-(p-nitrophenyl)-ethyl)-6,6'-dimethyl-2,2'-bipyridine (28)

4,4'-Bis(2-phenylethyl)-6,6'-dimethyl-2,2'-bipyridine (27) (3.0 g, 7.6 mmoles) was dissolved in tetrahydrofurane (30 ml). 65% nitric acid (0.81 g) was added and the solution was evaporated. Concentrated sulfuric acid (26 ml) was added and the solution was stirred at 60° C. for 30 minutes. The reaction mixture was poured slowly onto 200 ml ice. Water solution was neutralized with solid sodium carbonate and then extracted with chloroform/ethanol solution. The organic phase was dried and evaporated. The product was purified by means of flash chromatography.

Yield: 34%

UV (in ethanol): 285 nm, 251 nm $^1$HNMR (60 MHz, CDCl$_3$): 2.59 (s, 6H); 3.05 (bs, 6H); 6.95 (s, 2H); 7.34 (d, 4H, J=9 Hz); 8.08 (s, 2H); 8.15 (d, 4H, J=9 Hz)

EXAMPLE 29

Procedures for introducing reactive halomethyl groups into bipyridines or bipyrimidines A) GENERAL PROCEDURE FOR DIRECT HALOGENATION OF DIMETHYL COMPOUNDS WITH N-HALOSUCCINIMIDES Ref. G. R. Newkome et al., J. Org. Chem., 48, 5112–5114 (1983)

Dimethyl compound (4.0 mmoles), was dissolved in carbon tetrachloride (100 ml). N-Bromosuccinimide (9.0 mmoles) and a catalytic amount of dibenzoyl peroxide were added and the mixture was refluxed overnight. The mixture was filtered and the solution was evaporated to dryness. The product was purified by flash chromatography.

B) GENERAL PROCEDURE FOR SYNTHESIS OF BIS HALOMETHYL BIPYRIDINES AND BIPYRIMIDINES VIA BIS ACETATE (Scheme II)

i) General procedure for N,N'-dioxide synthesis Ref. W. Sont et al. Org. Prep. Proced. Int. 243–244 (1980)

A 6,6'-Dimethyl-2,2'-bipyridine (or an analogous dimethyl-bipyrimidine) (5 mmoles) was dissolved in chloroform (100 ml). m-Chloroperbenzoic acid (15 mmoles) was added and the solution was stirred for 3 hours. After extraction with saturated sodium hydrogen carbonate solution, the chloroform phase was dried and evaporated to dryness. The product was purified by means of flash chromatography.

ii) General procedure for diacetate synthesis from N,N-dioxide Ref. G. R. Newkome, J. Org. Chem., 47, 4116–4120 (1982)

A 6,6'-Dimethyl-2,2'-bipyridine-N,N'-dioxide (3 mmoles) was dissolved in acetic anhydride (20 ml) and the solution was refluxed for 0.5 hours. Acetic anhydride was evaporated and the residue was partitioned between saturated sodium hydrogen carbonate and chloroform. The organic phase was dried, evaporated and the product was purified by flash chromatography.

iii) General procedure for dialcohol synthesis

Diacetate (1 mmol) was dissolved in acetone (10 ml) and 1N sodium hydroxide (10 ml) was added. After stirring for 1 hour at room temperature the solution was neutralized with hydrochloric acid. Acetone was evaporated and the water phase was extracted with chloroform. Chloroform was evaporated and the product was purified by flash chromatography.

iv) General procedure for dibromide or dichloride synthesis from dialcohol

Dialcohol (1 mmol) was dissolved in chloroform (15 ml) and phosphorus tribromide or phosphorus trichloride (1.5 mmol) was added. After refluxing for two hours the mixture was cooled and extracted with saturated sodium hydrogen carbonate. The chloroform phase was dried and evaporated to dryness. Purification by flash chromatography gave pure dibromide.

C) GENERAL PROCEDURE FOR INTRODUCTION OF BIS-CHLOROMETHYL GROUPS DIRECT FROM DI N,N'-OXIDE (Scheme II)

Ref. T. Sakamoto et al., Heterocycl., 20, 991–994 (1983)

A 6,6'-Dimethyl-2,2'-bipyridine-N,N'-dioxide (1 mmole) (or an analogous bipyrimidine-N,N'-dioxide) was dissolved in 1,4-dioxane (20 ml) and phosphorus oxychloride (7 mmoles) was added. The mixture was refluxed for two hours and then evaporated to dryness. The product was purified by flash chromatography.

EXAMPLE 30

6,6'-Bis(chloromethyl)-2,2'-bipyridine (30)

Ref. G. R. Newkome et al., J. Org. Chem., 48, 5112–5114 (1983)

According to general direct halogenation procedure of Example 29A 6,6'-dimethyl-2,2'-bipyridine (1) (0.26 g, 2.3 mmoles), N-chlorosuccinimide (0.47 g, 5.5 mmoles), dibenzoylperoxide (3.6 mg) and tetrachloromethane (7.2 ml) were refluxed for 24 hours. The mixture was filtered and the solvent was evaporated. The product was purified by flash chromatography (silica, cyclohexane/methylene chloride 9:1).

Yield: 12%

UV (in ethanol): 287 nm, 238 nm $^1$HNMR (400 MHz, CDCl$_3$): 4.73 (s, 4H); 7.47 (d, 2H, J=7.5 Hz); 7.80 (t, 2H, J=7.5 Hz); 8.38 (d, 2H, J=7.5 Hz)

EXAMPLE 31

Scheme 14

4-Bromo-6,6'-bis(bromomethyl)-2,2'-bipyridine (31)

Using the general procedure (Example 29 A) for halogenation of dimethyl compounds with N-halosuccinimides and using (19) as a starting material.

UV (in ethanol): 290 nm $^1$HNMR (400 MHz, CDCl$_3$): 4.56 (s, 3H); 4.62 (s, 3H); 7.49 (dd, 1H, J=7.8 & 1.0 Hz); 7.63 (d, 1H, J=1.7 Hz); 7.82 (t, 1H, J=7.8 Hz); 8.35 (dd, 1H, J=7.8 & 1.0 Hz); 8.57 (d, 1H, J=1.7 Hz)

EXAMPLE 32

Scheme 9

4-(2-benzoyloxyethoxy)-6,6'-bis(bromomethyl)-2,2'-bipyridine (32)

Using the general procedure for halogenation of dimethyl compounds with N-halosuccinimides (Example 29 A) and compound (25) as a starting material Yield: 20%

$^1$HNMR (60 MHz, CDCl$_3$): 4.54 (s, 2H); 4.59 (s, 2H); 4.43–4.73 (m, 4H); 7.02 (d, 1H, J=2 Hz); 7.43 (dd, 1H, J=1 & 8 Hz); 7.36–7.56 (m, 3H); 7.78 (t, 1H, J=8 Hz);

7.99 (d, 1H, J=2 Hz); 7.99–8.15 (m, 2H); 8.38 (dd, 1H, J=1 & 8 Hz)

EXAMPLE 33

Scheme 10 i) 4,4'-Bis-(2-(p-nitrophenyl)-ethyl)-6,6'-dimethyl-2,2'-bipyridine-N,N-dioxide (33)

Using the general procedure of Example 29 B i), applying it to compound (28)
Yield: 46%
UV (in ethanol): 269 nm
$^1$HNMR (60 MHz, CDCl$_3$): 2.53 (s, 6H); 3.00 (bs, 8H); 7.12 (bs, 4H); 7.30 (d, 4H, J=9 Hz); 8.17 (d, 4H, J=9 Hz)

ii) 4,4'-Bis(2-(p-nitrophenyl)-ethyl)-6,6'-bis(acetoxymethyl)-2,2'-bipyridine (34)

Using the general procedure for diacetate synthesis according to Example 29 B ii) starting from N,N'-dioxide (33)
Yield: 54%
UV (in ethanol): 286 nm, 251 nm
$^1$HNMR (60 MHz, CDCl$_3$): 2.17 (s, 6H); 3.09 (bs, 8H); 5.27 (s, 4H); 7.12 (s, 2H), 7.34 (d, 4H, J=9 Hz); 8.16 (d, 4H, J=9 Hz); 8.23 (s, 2H)

iii) 4,4'-Bis(2-(p-nitrophenyl)-ethyl)-6,6'-bis(hydroxymethyl)-2,2'-bipyridine (35)

Using the general procedure for diol synthesis (Example 29 B iii) and compound (34) as a starting material
Yield: 90%
UV (in ethanol): 284 nm
$^1$HNMR (60 MHz, CDCl$_3$): 3.10 (bs, 8H); 4.81 (s, 4H); 7.21 (s, 2H); 7.34 (d, 4H, J=9 Hz); 8.17 (d, 4H, J=9 Hz); 8.17 (s, 2H)

iv) 4,4'-Bis(2-(p-nitrophenyl)-ethyl)-6,6'-bis(-chloromethyl)-2,2'-bipyridine (36)

Using the general procedure of Example 29 B iv) applying it to the compound (35) as a starting material
Yield: 36%
UV (in ethanol): 278 nm, 253 nm
$^1$HNMR (60 MHz, CDCl$_3$): 3.10 (bs, 8H); 4.70 (s, 4H); 7.26 (s, 2H); 7.34 (d, 4H, J=9 Hz); 8.17 (d, 4H, J=9 Hz); 8.24 (s, 2H)

EXAMPLE 34 i) 2,2'-Dimethyl-4,4'-bipyrimidine-N,N'-dioxide (37)

The synthesis was carried out as according to the general description in Example 29 B i).

2,2'-Dimethyl-4,4'-bipyrimidine (150 mg, 0.81 mmoles) (obtained according to F. Effenberger, Chem. Ber. 98, 2260–2265 (1986) see scheme 7) was dissolved in chloroform (2 ml). m-Chloroperbenzoic acid (420 mg, 2.4 mmoles) dissolved in chloroform (5 ml) was added slowly and the mixture was stirred overnight. Solvent was evaporated and the product was purified by flash chromatography.
Yield: 72%
UV (in ethanol): 368 nm, 295 nm
$^1$HNMR (400 MHz, CDCl$_3$+CH$_3$OH): 2.81 (s, 6H); 8.29 (d, 2H, J=7 Hz); 8.51 (d, 2H, J=7 Hz)

ii) 2,2'-Bis(chloromethylene)-4,4'-bipyrimidine (38)

The synthesis was carried out as according to the general description in Example 29 C.

2,2'-dimethyl-4,4'-bipyrimidine-N,N'-dioxide (70 mg, 0.32 mmoles), phosphorus oxychloride (300 mg, 2.0 mmoles) and 1,4-dioxane (7 ml) were refluxed for four hours. The solvent was evaporated and the product was purified by short column chromatography (5% methanol/chloroform)
Yield: 41%
UV (in ethanol): 285 nm, 276 nm
$^1$HNMR (400 MHz, CDCl$_3$): 4.85 (s, 4H); 8.41 (d, 2H, J=5 Hz); 9.00 (d, 2H, J=5 Hz)

EXAMPLE 35

4,4'-Dimethyl-2,2'-bipyrimidine-N,N'-dioxides (39)

According to the procedure of Example 29 B i).

4,4'-Dimethyl-2,2'-bipyrimidine (3) (210 mg, 1.13 mmoles) and m-chloroperbenzoic acid (1.4 g, 8.4 mmoles) were dissolved in chloroform (15 ml) and refluxed for five hours. The undissolved m-chloroperbenzoic acid was filtered out and the products (-three different N,N'-dioxides) were purified by means of flash chromatography.

Isomer 1

Yield: 29 mg
UV (in ethanol): 312 nm, 274 nm
$^1$HNMR (60 MHz, CDCl$_3$): 2.61 (s, 6H); 7.42 (d, 2H, J=5 Hz); 8.26 (d, 2H, J=5 Hz)

Isomer 2

Yield: 50 mg
UV (in ethanol): 316 nm, 272 nm
$^1$HNMR (60 MHz, CDCl$_3$): 2.59 (s, 6H); 7.44 (d, 1H, J=5 Hz); 7.44 (d, 1H, J=7 Hz); 8.28 (d, 1H, J=5 Hz); 8.49 (d, 1H, J=7 Hz)

Isomer 3

Yield: 32 mg
UV (in ethanol): 320 nm, 273 nm
$^1$HNMR (60 MHz, CDCl$_3$): 2.59 (s, 6H); 7.29 (d, 2H, J=7 Hz); 8.47 (d, 2H, J=7 Hz)

ii) 4,4'-Bis(chloromethylene)-2,2'-bipyrimidine (40)

According to the procedure of Example 29 C 4,4'-dimethyl-2,2'-bipyrimidine-N,N'-dioxide (39) (150 mg, 0.23 mmoles) (isomer 2) was dissolved in 1,4-dioxane (4 ml) and phosphorus oxychloride (400 μl, 1.6 mmoles) was added. The mixture was refluxed for two hours and then evaporated to dryness. Some ethanol was added and the mixture was evaporated again. The product was purified by flash chromatography (silica, 0–5% methanol/chloroform)
Yield: 31%
UV (in ethanol): 248 nm
$^1$HNMR (400 MHz, CDCl$_3$): 4.85 (s, 4H); 7.76 (d, 2H, J=5 Hz); 9.09 (m, 2H)

Both of the other isomeric N,N'-dioxides gave the same dichloride under identical conditions.

EXAMPLE 36

Scheme 6

Bis(6-bromomethyl-2-pyridyl)ketone (41)

Bis(6-hydroxymethyl-2-pyridyl)ketone (14) (410 mg, 1.68 mmoles) suspended in dichloromethane (15 ml) was stirred at room temperature in a 50 ml round bottom flask. Phosphorus tribromide (1.82 g, 6.72 mmoles) was added at once and the mixture was refluxed for 5 min. The cooled mixture was partitioned between saturated sodium hydrogen carbonate and chloroform. The organic phase was collected, evaporated, coevaporated with toluene, and purified by flash chromatography using chloroform as solvent.

Yield: 87%
UV (in dichloromethane): 282 nm
$^1$HNMR (60 MHz, CDCl$_3$); 4.55 (s, 4H); 8.16–7.22 (m, 6H)

EXAMPLE 37

Scheme 12

L-Lysine ethyl ester (42)

Thionyl chloride (5.0 ml, 8.06 g, 68 mmoles) was dropped into 500 ml of icecooled dry ethanol. The stirred mixture was kept for 20 min at this temperature and L-lysine hydrochloride (20 g, 109 mmoles) was added.

The mixture was then refluxed for 3 h and concentrated to a volume of about 200 ml. 200 ml of diethylether was added and the crystallized product filtered off. Yield: 97% dihydrochloride

EXAMPLE 38

Scheme 12

ω-N-(4-Nitrobenzoyl)-L-lysine ethyl ester (43)

L-lysine HCl (5 g, 27.4 mmoles) dissolved in 50 ml of water was titrated with 5M NaOH to pH 10.5. 4-Nitrobenzoyl chloride (6.6 g, 36 mmoles) in dioxane (50 ml) and 5M NaOH were slowly added keeping the vigorously stirred reaction mixture at pH 10.5.

After complete addition and disappearance of the pink color the reaction mixture was acidified with conc. HCl to pH 2 and extracted four times with diethylether. The aqueous phase was concentrated to dryness, coevaporated twice with 200 ml of dry ethanol and suspended in 250 ml of dry ethanol previously treated with 10 ml of thionyl chloride. The mixture was refluxed for 3 h, filtered and evaporated. The residual material was partitioned between saturated sodium hydrogen carbonate and chloroform/ethanol 1:1 and the organic phase was dried over magnesium sulphate yielding a crude product which was purified by flash chromatography using 5% EtOH/chloroform as eluent.

Yield: 12%
$^1$HNMR (60 MHz, CDCl$_3$): 8.25 (d, 2H, J=9 Hz); 7.93 (d, 2H, J=9 Hz); 6.87 (s, broad, 1H); 4.17 (q, 2H, J=7 Hz); 3.30–3.60 (m, 8H); 1.24 (t, 3H, J=7 Hz)

EXAMPLE 39

Scheme 12

α-N-(Methoxycarbonylmethyl)-ω-N-(4-nitrobenzoyl)-L-lysine ethyl ester (44)

Compound (43) (0.54 g, 1.7 mmoles) was coevaporated with toluene, dissolved in dry acetonitrile (10 ml) and bromacetic acid methylester (0.265 g, 1.7 mmoles) was added followed by pulverized dry sodium carbonate (2.0 g). The mixture was refluxed for 3 h.

Filtration of the inorganic salts and evaporation of the acetonitrile gave an oily crude product which was purified by flash chromatography.

Yield: 68%
$^1$HNMR (60 MHz, CDCl$_3$): 8.25 (d, 2H, J=9 Hz); 7.93 (d, 2H, J=9 Hz); 6.63 (s, broad, 1H); 4.13 (q, 2H, J=7 Hz); 3.68 (s, 3H); 3.30–3.60 (m, 3H); 1.40–1.75 (m, 7H); 1.24 (t, 3H, J=7 Hz).

EXAMPLE 40

Scheme 12

ω-N-Monomethoxytrityl-L-lysine ethyl ester (45)

Dry triethylamine (1.8 ml, 18 mmoles) was added to a suspension of (42) (1.5 g, 6 mmoles) in 20 ml of dry pyridine. To this mixture stirred at RT, solid monomethoxytrityl chloride (1.96 g, 6 mmoles) (MMTrCl) was added in small portions during a period of 1 h whereupon the mixture was stirred for additional 2 h. A standard sodium bicarbonate work-up followed by extraction with chloroform yielded a crude product contaminated by α-MMTr isomer.

The pure title product was easily isolated by flash column chromatography due to the large Rf difference between the isomers.

Yield: 48%
$^1$HNMR (400 MHz, CDCl$_3$): 7.5–6.75 (m, 14H); 4.18 (q, 2H, J=7 Hz); 3.78 (s, 3H); 3.45–3.37 (m, 1H); 2.14–2.10 (t, 2H, J=7 Hz); 1.75–1.35 (m, 9H); 1.26 (t, 3H, J=7 Hz)

EXAMPLE 41

Scheme 12

α-N-(Methoxycarbonylmethyl)-ω-N-monomethoxytrityl-L-lysine ethyl ester (46)

A partially protected L-lysine derivative (45) (1.0 g, 2.13 mmoles) was converted to product (46) using the method described in Example 39.

Yield: 70%
$^1$HNMR (400 MHz, CDCl$_3$): 7.46–6.77 (m, 14H); 4.19–4.14 (q, 2H); 3.77 (s, 3H); 3.70 (s, 3H); 3.31–3.45 (q, 2H, J=7 Hz); 3.22–3.25 (t, 1H); 2.09–2.12 (t, 2H); 1.35–1.70 (m, 6H); 1.23–1.27 (t, 3H)

EXAMPLE 42

Scheme 12

ω-N-Trifluoroacetyl-L-lysine ethyl ester (47)

Compound (42) (2.0 g, 8.1 mmoles), dissolved in 10 ml of dry ethanol was treated with dry triethylamine (4.09 g, 40.4 mmoles). Ethyl trifluoroacetate (1.5 g, 10.5 mmoles) was added to the stirred suspension formed, and the mixture was refluxed for 6 h.

All volatile substances were then evaporated and the residue partitioned between saturated sodium hydrogen carbonate and chloroform/ethanol 1:1.

The combined organic phase (5×60 ml) was evaporated, coevaporated with toluene and flash chromatographed to get the title product in the form of a colorless oil.

Yield: 87%
$^1$HNMR (400 MHz, CDCl$_3$): 7.10 (t, 1H, exchangeable); 4.21–4.16 (q, 2H); 3.45–3.40 (m, 1H); 3.38–3.31 (m, 2H); 1.84 (s, 2H, exchangeable); 1.82–1.40 (m, 6H); 1.28 (t, 3H)

EXAMPLE 43

Scheme 12

α-N-(Methoxycarbonylmethyl)-ω-N-trifluoroacetyl-L-lysine ethyl ester (48)

L-lysine derivative (47) (1.0 g, 3.7 mmoles) was converted to the product (48) in a method analogous to Example 39.

Yield: 83%

¹HNMR (60 MHz, CDCl₃+CD₃OD): 4.4-4.0 (q, 2H); 3.68 (s, 3H); 3.5-3.1 (m, 5H); 1.8-1.4 (m, 6H); 1.23 (t, 3H)

EXAMPLE 44

Scheme 12

ω-N-(4-Hydroxybutyryl)-L-lysine ethyl ester (49)

L-lysine ethyl ester, 2 HCl (42) (2 g, 8.1 mmoles) in 30 ml of dry ethanol was treated with dry triethylamine (5.63 ml, 40.5 mmoles) and γ-butyrolactone (0.7 g, 8.1 mmoles) and the suspension obtained was refluxed for 3 h.

Evaporation of volatile substances and coevaporation with toluene yielded a crude product which was purified by flash chromatography using 20% methanol/chloroform as solvent.

Yield: 73%

¹HNMR (400 MHz, CDCl₃+CD₃OD): 4.30-4.22 (q, 2H); 3.72-3.77 (m, 1H); 3.58-3.65 (t, 2H); 3.18-3.28 (m, 2H); 2.30-2.36 (t, 2H); 1.40-2.00 (m, 8H); 1.28-1.34 (t, 3H)

EXAMPLE 45

Scheme 12

α-N-(Methoxycarbonylmethyl)-ω-N-(4-hydroxybutyryl)-L-lysine ethyl ester (50)

Compound (49) (1.22 g, 4.68 mmoles) in 20 ml of dry acetonitrile was converted to product (50) in a reaction analogous to that in Example 39.

Yield: 64%

¹HNMR (400 MHz, CDCl₃): 6.25 (s, broad, 1H); 4.16-4.21 (q, 2H); 3.73 (s, 3H); 3.67-3.69 (t, 2H); 3.33-3.49 (m, 2H); 3.20-3.30 (m, 3H); 2.34-2.37 (t, 2H); 1.40-1.90 (m, 8H); 1.26-1.30 (t, 3H)

EXAMPLE 46

Scheme 13

General Procedure for Synthesis of Unfunctionalized Tetraester

Bis(nalomethyl) compound (1.0 mmole), di-t-butyl, diethyl or dimethyl iminodiacetate (2.5 mmoles), sodium carbonate (250 mg) and acetonitrile (10 ml) are refluxed overnight. The mixture is filtered, solvent is evaporated and the product is purified by flash chromatography.

EXAMPLE 47

Scheme 9

4-(2-benzoyloxyethoxy)-6,6'-bis(N,N-bis(ethoxycarbonylmethyl)aminomethyl)-2,2'-bipyridine (51)

Using the general procedure of tetraester synthesis of Example 46 and compound (32) as a starting material.

Yield: 63%

¹HNMR (60 MHz, CDCl₃): 1.23 (t, 12H, J=7 Hz); 3.65 (s, 8H); 4.10 (s, 4H); 4.16 (q, 8H, J=7 Hz); 4.50-4.77 (m, 4H); 7.24 (d, 1H, J=2 Hz); 7.56 (d, 1H, J=8 Hz); 7.39-7.60 (m, 3H); 7.79 (t, 1H, J=8 Hz); 7.97-8.16 (m, 2H); 8.02 (d, 1H, J=2 Hz); 8.31 (d, 1H, J=8 Hz)

EXAMPLE 48

Scheme 9

4-(2-hydroxyethoxy)-6,6'-bis(N,N-bis(ethoxycarbonylmethyl)aminomethyl)-2,2'-bipyridine (52)

4-(2-benzoyloxyethoxy)-6,6'-bis(N,N-bis(ethoxycarbonylmethyl)aminomethyl-2,2'-bipyridine (220 mg, 0.31 mmoles) was added to a solution containing ethanol (20 ml) and thionyl chloride (1.5 ml). The mixture was refluxed overnight and then evaporated. The residue was dissolved in chloroform and it was extracted with saturated sodium bicarbonate solution. The product was purified by means of flash chromatography (silica, 0-5% methanol/chloroform).

Yield: 36%

¹HNMR (60 MHz, CDCl₃): 1.25 (t, 12H, J=7 Hz); 3.65 (s, 8H); 4.11 (s, 4H); 4.17 (q, 8H, J=7 Hz); 3.99-4.35 (m, 4H); 7.21 (d, 1H, J=2 Hz); 7.54 (dd, 1H, J=2 & 7 Hz); 7.77 (t, 1H, J=7 Hz); 7.90 (d, 1H, J=2 Hz); 8.28 (dd, 1H, J=2 & 7 Hz)

EXAMPLE 49 as in Scheme 13

4,4'-Bis(N,N-bis(t-butoxycarbonylmethyl)aminomethyl)-2,2'-bipyrimidine (53)

4,4'-Bis(chloromethyl)-2,2'-bipyrimidine (18.0 mg, 0.0793 mmoles), di-t-butyl iminodiacetate (76.3 mg, 0.31 mmoles), sodium carbonate (210 mg) and acetonitrile (3 ml) were refluxed overnight. The mixture was filtered, the solvent was evaporated and the product was purified by flash chromatography (silica, 0-5% methanol/chloroform).

Yield: 47%

UV (in ethanol): 244 nm

¹HNMR (60 MHz, CDCl₃): 1.45 (s, 36H); 3.50 (s, 8H); 4.23 (s, 4H); 7.97 (d, 2H, J=5 Hz); 8.97 (d, 2H, J=5 Hz)

EXAMPLE 50

Scheme 14

4-Bromo-6,6'-bis(N,N-bis(t-butoxycarbonylmethyl)aminomethyl)-2,2'-bipyridine (54)

Using the general procedure of Example 46 and compound (31) as a starting material.

UV (in ethanol): 291 nm, 242 nm

¹HNMR (400 MHz, CDCl₃): 1.47 (s, 36H); 3.52 (s, 8H); 4.10 (s, 2H); 4.11 (s, 2H); 7.66 (d, 1H, J=7.6 Hz); 7.78 (t, 1H, J=7,6 Hz); 7.83 (s, 1H); 8.27 (d, 1H, J=7.6 Hz); 8.49 (s, 1H)

EXAMPLE 51

2,2'-Bis(N,N-bis(t-butoxycarbonylmethyl)-aminomethyl)-4,4'-bipyrimidine (55)

Using the general procedure of Example 46 and compound (38) as a starting material.

UV (in ethanol): 276 nm

¹HNMR (400 MHz, CDCl₃): 1.45 (s, 36H); 3.68 (s, 8H); 4.34 (s, 4H); 8.34 (d, 2H, J=5.1 Hz); 8.91 (d, 2H, J=5.1 Hz)

EXAMPLE 52

6,6'-Bis(N,N-bis(ethoxycarbonylmethyl)-aminomethyl-2-pyridyl)ketone (56)

This compound has been prepared using the general procedure of Example 46, applying it to compound (41) as a starting material.
Yield: 82%
UV (in $CH_2Cl_2$): 280 nm
$^1$HNMR (60 MHz, $CDCl_3$): 1.21 (t, 12H); 3.60 (s, 8H); 4.08 (s, 4H); 4.15 (q, 8H); 7.95–7.80 (m, 6H)

EXAMPLE 53

Scheme 13

General Procedure for the Synthesis of Reactive Ligand or Chelate Employing Derivatives of $\alpha, \omega$ Diaminoacids as Starting Material a) The appropriate dihalomethyl bipyridine or bipyrimidine (1 mmol) in dry acetonitrile (10 ml) is reacted with 1 mmol of one of compounds (44), (46), (48) or (50) in the presence of 2 g powderized dry sodium carbonate at room temperature with vigorous stirring. After overnight stirring the resulting mixture composed of unreacted dihalomethyl derivative, monohalomethyl diester, and tetraester is evaporated, coevaporated with toluene and flash chromatographed to give pure monohalomethyl diester.

b) The obtained monohalomethyl diester (0.2 mmoles) is coevaporated with dry acetonitrile, dissolved in 3 ml of acetonitrile, and 1 g of powderized sodium carbonate is added followed by iminodiacetic acid diethyl ester (0.25 mmoles). The mixture is refluxed overnight, filtered and evaporated. The desired functionalized tetraester is obtained after short column chromatography.

c) If compound (44) is used as a starting material in Example 53 a) the nitro group has to be reduced to amino prior to ester group hydrolysis and chelate formation. This is performed in the following way:
Solid sodium borohydride (0.3 mmoles) is added to the mixture from Example 53 b) followed by 0.2 g palladium on carbon (10%) in 5 ml of dry ethanol. The resultant mixture is stirred at room temperature for 10 min and partitioned between saturated sodium hydrogen carbonate and chloroform. The evaporated organic extracts are flash chromatographed to yield the respective tetraester containing a reactive amino group.

d) If compound (50) is used as a starting material in Example 53 a) its side chain hydroxyl group has to be activated in order to allow subsequent coupling of such a ligand to the other hydroxyl containing materials. This can be performed in several ways known to those who are skilled in the art. Here we present one of the possibilities which can be applied for instance to direct coupling of an activated ligand to oligonucleotides synthesized by solid phase method.
2-Cyanoethyl-N,N-diisopropylaminophosphochloridate (2 mmol) is added to a mixture of hydroxytetraester from Example 53 b) and diisopropylethylamine (4.6 mmoles) in anhydrous dichloromethane (10 ml). After 15 min of stirring at room temperature the mixture is washed with cold sodium hydrogen carbonate, extracted with dichloromethane, evaporated and purified by silica gel column chromatography using petroleum ether/triethylamine 9:1 as the eluting solvent.

EXAMPLE 54

Scheme 13

General Procedure for Tetraacid Synthesis Starting from Diethyl or Tetraethyl Ester Bis(N,N-bis(ethoxycarbonylmethyl)aminomethyl) derivative (0.25 mmoles) was dissolved in acetone (10 ml). 1N sodium hydroxide solution (10 ml) was added. After 1 hour the solution was neutralized with concentrated hydrochloric acid and most of the salts were precipitated by adding acetone. After filtration the solution was evaporated to dryness.

EXAMPLE 55

Scheme 13

General Procedure for Tetraacid Synthesis Starting from Tetra-t-Butyl Ester

Bis(N,N-bis(t-butoxycarbonylmethyl)aminomethyl) derivative (0.25 mmoles) was dissolved in trifluoroacetic acid (10 ml). After five hours of stirring trifluoroacetic acid was evaporated and some diethyl ether was added. The product was filtered and dried.

EXAMPLE 56

General Procedure for Europium or Terbium Chelate Synthesis

Tetra acid (0.20 mmoles) was dissolved in water and the pH was adjusted to 5.0–5.5. Europium or terbium chloride (0.20 mmoles) dissolved in water was added. After stirring for 30 minutes the pH was adjusted to 8.0 and the precipitate was filtered out. Most of the water was evaporated under reduced pressure and the product was precipitated by adding acetone.

EXAMPLE 57

Scheme 14

Procedure for Phenylethynylation of Bipyridine Tetraesters

Ref. J. Kankare et al., EP-A-203,047.

4-Bromo-6,6'-bis(N,N-bis(t-butoxycarbonylmethyl)aminomethyl)-2,2'-bipyridine (750 mg, 1.0 mmole) or the corresponding 4,4'-dibromo derivative (414 mg, 0.50 mmoles), bis(triphenylphosphine)palladium(II) chloride (14.0 mg, 0.020 mmoles) and copper(I) iodide (7.6 mg, 0.040 mmoles) were dissolved in dry triethylamine (15 ml). After bubbling nitrogen gas through the system for 10 min substituted alkyne (1.2 mmoles) was added. After stirring at 40°–50° C. usually for 3 hours the solution was filtered and the precipitate was washed with dry triethylamine. Solvents were evaporated and the residue was dissolved in chloroform. After extraction with water the chloroform phase was dried and evaporated. The product was purified by means of flash chromatography.

4-(p-Aminophenylethynyl)-6,6'-bis(N,N-bis(t-butoxycarbonylmethyl)aminomethyl)-2,2'-bipyridine (57)

Using p-aminophenyl acetylene as the substituted alkyne
UV (in ethanol): 338 nm, 314 nm, 294 nm, 231 nm
$^1$HNMR (400 MHz, $CDCl_3$): 1.47 (s, 18H); 1.48 (s, 18H); 3.53 (s, 4H); 3.55 (s, 4H); 4.12 (s, 2H); 4.13 (s, 2H); 6.65 (d, 2H, J=8.7 Hz); 7.36 (d, 2H, J=8.7 Hz); 7.64 (d, 1H, J=7.8 Hz); 7.67 (d, 1H, J=1.4 Hz); 7.78 (t, 1H, J=7.8 Hz); 8.30 (d, 1H, J=7.8 Hz); 8.37 (d, 1H, J=1.4 Hz)

EXAMPLE 58

Scheme 14

4-(p-Aminophenylethynyl)-6,6'-bis(N,N-bis(carboxymethyl)aminomethyl)-2,2'-bipyridine (58)

Using the method of Example 55 with compound (57) as a starting material.

UV (in water): 297 nm $^1$HNMR (400 MHz, DMSO): 3.68 (s, 4H); 3.70 (s, 4H); 4.22 (s, 2H); 4.30 (s, 2H); 6.62 (d, 2H, J=8.0 Hz); 7.33 (d, 2H, J=8.0 Hz); 7.65 (s, 1H); 7.66 (d, 1H, J=7.5 Hz); 8.01 (t, 1H, J=7.5 Hz); 8.29 (d, 1H, J=7.5 Hz); 8.33 (s, 1H)

EXAMPLE 59

Scheme 14

4-(p-Aminophenylethynyl)-6,6'-bis(N,N-bis(carboxymethyl)aminomethyl)-2,2'-bipyridine as europium chelate (59)

The synthesis was carried out using the general procedure for europium chelate synthesis according to Example 56 applied to compound (58)

UV (in water): 317 nm, 240 nm

EXAMPLE 60

General Procedure for Isothiocyanate Chelate Synthesis

Ref. Mikola et al., EP-A-0139,675

Amino chelate (0.05 mmoles) was dissolved in 3 ml water and sodium hydrogen carbonate (20 mg) was added. This chelate solution was added slowly to the thiophosgene solution (20 μl in chloroform (3 ml)) and stirred for 30 minutes. The phases were separated and the aqueous phase was extracted with chloroform. The aqueous phase was evaporated to a small volume and the product was precipitated with acetone and dried.

EXAMPLE 61

Scheme 14

4-(p-Isothiocyanatophenylethynyl)-6,6'-bis(N,N-bis(carboxymethyl)aminomethyl)-2,2'-bipyridine as europium chelate (60)

Using the isothiocyanate synthesis of Example 60 applied to chelate (59). UV (in water): 317 nm

EXAMPLE 62

Scheme 9

Synthesis of (61)-phosphitamidate derivative of compound (52)

This synthesis was carried out essentially according to the description of Example 53d) using compound (52) as a starting material.

Yield: 72%

$^1$HNMR (400 MHz, CDCl$_3$): 1.20 (d, 6H, J=2 Hz); 1.21 (d, 6H, J=2 Hz); 1.25 (t, 6H, J=7 Hz); 1.27 (t, 6H, J=7 Hz); 2.65 (t, 2H, J=5 Hz); 3.67 (s, 8H); 3.60–3.70 (m, 2H); 3.82–3.92 (m, 2H); 3.93–4.00 (m, 1H); 4.04–4.11 (m, 1H); 4.10 (s, 2H); 4.15 (s, 2H); 4.17 (q, 8H, J=7 Hz); 4.30 (t, 2H, J=5 Hz); 7.18 (d, 1H, J=2 Hz); 7.59 (d, 1H, J=8 Hz); 7.76 (t, 1H, J=8 Hz); 7.89 (d, 1H, J=2 Hz); 8.29 (d, 1H, J=8 Hz) $^{31}$PNMR (CDCl$_3$): 148.9 (s)

EXAMPLE 63

Scheme 10

4,4'-(Bis(2-(p-nitrophenyl)-ethyl)-6,6'-bis(N,N-bis(ethoxycarbonylmethyl)aminomethyl)-2,2'-bipyridine (62)

The synthesis was carried out using the general method for tetraester synthesis as in Example 46 applied to compound (36)

Yield: 45%

UV (in ethanol): 282 nm $^1$HNMR (60 MHz, CDCl$_3$): 1.25 (t, 12H, J=7 Hz); 3.09 (bs, 8H); 3.62 (s, 8H); 4.12 (s, 4H); 4.18 (q, 8H, J=7 Hz); 7.35 (d, 4H, J=9 Hz); 7.43 (s, 2H); 8.15 (d, 4H, J=9 Hz); 8.16 (s, 2H)

EXAMPLE 64

Scheme 10

4,4'-Bis(2-(p-aminophenyl)-ethyl)-6,6'-bis(N,N-bis(ethoxycarbonylmethyl)aminomethyl)-2,2'-bipyridine (63)

The synthesis was carried out essentially according to the description of Example 53 c), using compound (62) as a starting material.

Yield: 28%

$^1$HNMR (60 MHz, CDCl$_3$): 1.25 (t, 12H, J=7 Hz); 2.91 (bs, 8H); 3.70 (s, 8H); 4.12 (s, 4H); 4.18 (q, 8H, J=7 Hz); 6.64 (d, 4H, J=8 Hz); 6.99 (d, 4H, J=8 Hz); 7.30 (s, 2H); 8.10 (s, 2H)

EXAMPLE 65

Scheme 10

4,4'-Bis(2-(p-aminophenyl)-ethyl)-6,6'-bis(N,N-bis(carboxymethyl)aminomethyl)-2,2'-bipyridine (64)

The synthesis was carried out using the general method according to the description of Example 54 and using compound (63) as a starting material.

UV (in water): 300 nm, 289 nm, 235 nm $^1$HNMR (60 MH, DMSO): 3.00 (bs, 8H); 3.35 (s, 8H); 3.64 (s, 4H); 6.65 (d, 4H, J=8 Hz); 7.02 (d, 4H, J=8 Hz); 7.28 (s, 2H); 8.10 (s, 2H);

EXAMPLE 66

Scheme 10

4,4'-Bis(2-(p-aminophenyl)-ethyl)-6,6'-bis(N,N-bis(carboxymethyl)aminomethyl)-2,2'-bipyridine as europium chelate (65)

The synthesis was carried out using the general procedure for europium chelate synthesis (Example 56) with compound (64) as a starting material.

UV (in water): 310 nm, 299 nm, 234 nm

EXAMPLE 67

Scheme 10

4,4'-Bis(2-(p-isothiocyanatophenyl)-ethyl)-6,6'-bis(N,N-bis(carboxymethyl)aminomethyl)-2,2'-bipyridine europium chelate (66)

The synthesis was carried out using the general procedure for isothiocyanate chelate synthesis (Example 60) applied to compound (65).

UV (in water): 318 nm, 280 nm

EXAMPLE 68

Scheme 5

6,6'-Dimethyl-4,4'-diphenyl-2,2'-bipyridine (67)

Ref. F. Kroehnke, Synthesis, 1-24 (1976)

2.62 g (10.0 mmoles) 1,6-diphenyl-3,4-dioxo-butane-1,5-diene, 3.43 g (20 mmoles) acetonyl pyridinium chloride, 20 g ammonium acetate and 100 ml methanol were refluxed for four hours. After cooling to 0° C. the precipitated product was filtered and recrystallized from methanol.

Yield: 40%

UV (in ethanol): 302 nm, 246 nm $^1$HNMR (60 MHz, CDCl3): 2.70 (s, 6H); 7.41-7.79 (m, 12H); 8.50 (s, 2H)

EXAMPLE 69

Scheme 15A 6,6'-Bis(bromomethyl)-4,4'-diphenyl-2,2'-bipyridine (68)

This compound was synthesized according to the general procedure of Example 29 for halogenation of dimethyl compounds with N-halosuccinimides.

Yield: 32%

UV (in ethanol): 299 nm, 252 nm $^1$HNMR (60 MHz, CDCl$_3$): 4.71 (s, 4H); 7.45-7.74 (m, 12H); 8.68 (d, 2H, J=2 Hz)

EXAMPLE 70

Scheme 15A 4,4'-Diphenyl-6-(N-(methoxycarbonylmethyl)-N-(1-(5-(p-nitrobenzamido))-1-(ethoxycarbonyl)-pentyl)-aminomethyl)-6'-bromomethyl-2,2'-bipyridine (compound (69)) and
4,4'-diphenyl-6,6'-Bis(N-(methoxycarbonylmethyl)-N-(1-(5-(p-nitrobenzamido))-1-(ethoxycarbonyl)-pentyl)aminomethyl)-2,2'-bipyridine (compound (70))

The general procedure of Example 53a gave both diester and tetraester compounds when 6,6'-bis(bromomethyl)-4,4'-diphenyl-2,2'-bipyridine (68) and modified iminodiacetic acid ester (compound 44) were used in the ratio 1:1.2.

Compound (69)

Yield: 41%

$^1$HNMR (60 MHz, CDCl3): 1.26 (t, 3H, J=7 Hz); 1.56-1.90 (m, 6H); 3.30- 3.54 (m, 3H); 3.54 (s, 3H); 3.75 (s, 2H); 4.14 (s, 2H); 4.19 (q, 2H, J=7 Hz); 4.70 (s, 2H); 7.36-7.85 (m, 12H); 7.78 (d, 2H, J=9 Hz); 8.12 (d, 2H, J=9 Hz); 8.60 (d, 1H, J=2 Hz); 8.63 (d, 1H, J=2 Hz)

Compound (70)

Yield: 21%

$^1$HNMR (60 MHz, CDCl3): 1.28 (t, 6H, J=7 Hz); 1.56-1.90 (m, 12H); 3.28-3.50 (m 6H); 3.56 (s, 6H); 3.74 (s, 4H); 4.14 (s, 4H); 4.20 (q, 4H, J=7 Hz); 7.36-7.80 (m, 12H); 7.80 (d, 4H, J=9 Hz); 8.10 (d, 4H, J=9 Hz); 8.57 (d, 2H, J=2 Hz)

EXAMPLE 71

Scheme 15A 4,4'-Diphenyl-6-(N-(methoxycarbonylmethyl)-N-(1-(5-p-nitrobenzamido))-1-(ethoxycarbonyl)-pentyl)-aminomethyl)-6'-(N,N-bis(ethoxycarbonylmethyl)aminomethyl)-2,2'-bipyridine (71)

This compound was synthesized following the general procedure for tetraester synthesis according to Example 53b using compound (69) and diethyl iminodiacetate as starting materials.

Yield: 51%

UV (in ethanol): 300 nm, 252 nm $^1$HNMR (400 MHz, CDCl$_3$): 1.21 (t, 6H, J=7 Hz); 1.27 (t, 3H, J=7 Hz); 1.50-1.90 (m, 6H); 3.35-3.50 (m, 3H); 3.57 (s, 3H); 3.71 (s, 6H); 4.14 (q, 6H, J=7 Hz); 4.18 (s, 2H); 4.19 (s, 2H); 7.45-7.83 (m, 12H); 7.73 (d, 2H, J=8 Hz); 8.11 (d, 2H, J=8 Hz); 8.58 (d, 2H, J=2 Hz)

EXAMPLE 72

Scheme 15B 4,4'-Diphenyl-6,6'-bis(N-(methoxycarbonylmethyl)-N-(1-(5-(p-aminobenzamido))-1-(ethoxycarbonyl)-pentyl)aminomethyl)-2,2'-bipyridine (72)

Compound (70) was reduced with palladium on carbon and sodium borohydride according to the general description of Example 53c.

Yield: 76%

UV (in ethanol): 270 nm, 256 nm $^1$HNMR (60 MHz, CDCl$_3$): 1.25 (t, 6H, J=7 Hz); 1.43-1.87 (m, 6H); 3.22-3.52 (m, 6H); 3.61 (s, 6H); 3.71 (s, 4H); 4.16 (q, 4H, J=7 Hz), 4.19 (s, 4H); 6.55 (d, 4H, J=8 Hz); 7.38-7.91 (m, 12H), 7.53 (d, 4H, J=8 Hz); 8.62 (d, 2H, J=2 Hz)

EXAMPLE 73

Scheme 15

4,4'-Diphenyl-6-(N-(methoxycarbonylmethyl)-N-(1-(5-(p-aminobenzamido))-1-(ethoxycarbonyl)-pentyl)aminomethyl)-6'-(N,N-bis(ethoxycarbonylmethyl)aminomethyl)-2,2'-bipyridine (73)

This compound was produced in a synthesis analogous to that of Example 72 and using compound (71) as a starting material.

Yield: 79%

UV (In ethanol): 252 nm $^1$HNMR (60 MHz, CDCl$_3$): 1.25 (t, 9H, J=7 Hz); 1.47-1.87 (m, 6H); 3.25-3.47 (m, 3H); 3.61 (s, 3H); 3.69 (s, 4H); 3.71 (s, 2H); 4.16 (q, 6H, J=7 Hz); 4.22 (s, 4H); 6.57 (d, 2H, J=8 Hz); 7.39-7.91 (m, 12H); 7.53 (d, 2H, J=8 Hz); 8.60 (d, 1H, J=2 Hz); 8.63 (d, 1H, J=2 Hz)

EXAMPLE 74

Scheme 15

4,4'-Diphenyl-6,6'-bis(N-(carboxymethyl)-N-(1-(5-(p-aminobenzamido))-1-carboxypentyl)aminomethyl)-2,2'-bipyridine and corresponding europium chelate (74)

Using compound (72) as a starting material the title compound was obtained by means of the general procedure for hydrolysis of tetraesters (Example 55) and europium chelate formation (General Example 56).

UV (as sodium salt): 261 nm

UV (as Eu$^{3+}$ complex): 330 nm, 315 nm, 268 nm

EXAMPLE 75

Scheme 15

4,4'-Diphenyl-6-(N-(carboxymethyl)-N-(1-((5-(p-aminobenzamido))-1-carboxypentyl)aminomethyl)-6'-(N,N-bis(carboxymethyl)aminomethyl)-2,2'-bipyridine and corresponding europium chelate (75)

Using with compound (71) as a starting material the title compounds was obtained by means of the general procedures for hydrolysis of tetraesters (Example 55)

and europium chelate formation (as in General Example 56).

UV (as sodium salt): 310 nm, 256 nm
UV (as Eu$^{3+}$ complex): 330 nm, 315 nm, 261 nm

EXAMPLE 76

Scheme 16

4-Ethoxy-6,6'-bis(bromomethyl)-2,2'-bipyridine (76)

This compound was synthesized according to the general procedure of Example 29A for halogenation of dimethyl compounds with N-halosuccinimides, and using compound (22) as a starting material.

Yield: 19%
UV (in ethanol): 286 nm, 225 nm
$^1$HNMR (400 MHz, CDCl$_3$): 1.45 (t, J=7.0 Hz); 4.19 (q, J=7.0 Hz); 4.55 (s); 4.60 (s); 6.95 (d, J=2.3 Hz); 7.43 (dd, J=0.9 Hz & 7.6 Hz); 7.77 (t, J=7.6 Hz); 7.90 (d, J=2.3 Hz); 8.35 (dd, J=0.9 Hz & 7.6 Hz)

EXAMPLE 77

Scheme 16

4-Ethoxy-6-(N-(methoxycarbonylmethyl)-N-(1-(5-(p-nitrobenzamido))-1-(ethoxycarbonyl)-pentyl)-aminomethyl)-6'-bromomethyl-2,2'-bipyridine (77)

This compound was synthesized using the general procedure of Example 53a. 4-Ethoxy-6,6'-bis(bromomethyl)-2,2'-bipyridine (76) and modified iminodiacetic acid ester (compound 44) were used as starting materials.

Yield: 38%
UV (in ethanol): 286 nm, 220 nm
$^1$HNMR (400 MHz, CDCl$_3$): 1.30 (t, J=7 Hz); 1.45 (t, J=7 Hz); 1.55–1.68 (m); 1.75–1.83 (m); 3.45 (m); 3.50 (m); 3.55 (d, J=15 Hz); 3.64 (s); 3.66 (d, J=15 Hz); 3.94 (d, J=15 Hz); 4.03 (d, J=15 Hz); 4.18 (q, J=7 Hz); 4.19 (q, J=7 Hz); 4.58 (s); 6.83 (s); 7.45 (s); 7.62 (d, J=7 Hz); 7.76 (t, J=7 Hz); 8.00 (d, J=9 Hz); 8.25 (d, J=9 Hz); 8.28 (d, J=7 Hz); 8.35 (s)

EXAMPLE 78

Scheme 16

4-Ethoxy-6-(N-(methoxycarbonylmethyl)-N-(1-(5-(p-nitrobenzamido))-1-(ethoxycarbonyl)-pentyl)-aminomethyl-6'-(N,N-bis(ethoxycarbonylmethyl)-)aminomethyl-2,2'-bipyridine (78)

This compound was synthesized following the tetraester synthesis general procedure of Example 53b using compound (77) and diethyl iminodiacetate as starting materials.

Yield: 62%
UV (in ethanol): 287 nm, 222 nm
$^1$HNMR (400 MHz, CDCl$_3$): 1.26 (t, J=7 Hz); 1.28 (t, J=7 Hz); 1.46 (t, J=7 Hz); 1.59 (m); 1.76 (m); 3.35 (m); 3.49 (m); 3.58 (d, J=15 Hz); 3.65 (s); 3.66 (s); 3.67 (s); 3.71 (d, J=15 Hz); 3.96 (d, J=15 Hz); 4.05 (d, J=15 Hz); 4.09 (s); 4.14 (q, J=7 Hz); 4.17 (q, J=7 Hz); 6.88 (s); 7.15 (d, J=2 Hz); 7.50 (d, J=7 Hz); 7.75 (d, J=7 Hz); 7.83 (d, J=2 Hz); 8.01 (d, J=9 Hz); 8.24 (d, J=7 Hz); 8.26 (d, J=9 Hz)

EXAMPLE 79

Scheme 16

4-Ethoxy-6-(N-(methoxycarbonylmethyl)-N-(1-(5-(p-aminobenzamido))-1-(ethoxycarbonyl)-pentyl)-aminomethyl)-6'-(N,N-bis(ethoxycarbonylmethyl)-)aminomethyl)-2,2'-bipyridine (79)

This compound was synthesized using the nitrogroup reduction general procedure of Example 53c having compound (78) as a starting material.

Yield: 71%
UV (in ethanol): 286 nm, 222 nm
$^1$HNMR (400 MHz, CDCl$_3$): 1.26 (t, J=7 Hz); 1.28 (t, J=7 Hz); 1.46 (t, J=7 Hz); 1.60 (m); 1.75 (m); 3.41 (m); 3.44 (m); 3.54 (d, J=15 Hz); 3.62 (d, J=15 Hz); 3.64 (s); 3.69 (s); 3.92 (d, J=15 Hz); 4.01 (d, J=15 Hz); 4.16 (q, J=7 Hz); 4.17 (q, J=7 Hz); 6.30 (s); 6.64 (d, J=9 Hz); 7.16 (d, J=2 Hz); 7.50 (d, J=7 Hz); 7.63 (d, J=9 Hz); 7.78 (t, J=7 Hz); 7.80 (d, J=2 Hz); 8.24 (d, J=7 Hz)

EXAMPLE 80

Scheme 16

4-Ethoxy-6-(N-(carboxymethyl)-N-(1-(5-(p-aminobenzamido))-1-carboxypentyl)aminomethyl)-6'-(N,N-bis(-carboxymethyl)-aminomethyl)-2,2'-bipyridine (80) and corresponding europium chelate (81)

Compound (79) was hydrolyzed using the general method in Example 54 and the europium chelate was formed according to Example 56 starting from compound (80).

UV (as sodium salt in water): 295 nm, 286 nm, 225 nm
UV (as europium chelate in water): 308 nm, 290 nm, 230 nm

EXAMPLE 81

Scheme 16

4-Ethoxy-6-(N-(carboxymethyl)-N-(1-(5-(p-isothiocyanatobenzamido))-1-carboxypentyl)aminomethyl)-6'-(N,N-bis(carboxymethyl)-aminomethyl)-2,2'-bipyridine as europium chelate (82)

The amino group in compound (81) was converted to isothiocyanato group using the general procedure in Example 60.

UV (in water): 309 nm, 290 nm, 228 nm

EXAMPLE 82

Scheme 6

6-(N-(carboxymethyl)-N-(1-(5-(p-isothiocyanatobenzamido))-1-carboxypentyl)aminomethyl)-6'-N,N-bis(carboxymethyl)aminomethyl-2,2'dipyridyl ketone This compound was prepared using essentially the same procedure as for the synthesis of compound (82). Bis(6-bromomethyl-2-pyridyl)ketone (41) was subjected to the reaction with modified iminodiacetic acid (44) according to Example 77. Following the procedure of Examples 78→79→80 it was converted to an amino-form of europium chelate. The amino group was reacted with thiophosgene analogically to the procedure of Example 81 to form the active isothiocyanate chelate (83).

EXAMPLE 83

Fluorometric method employing lanthandde chelates of the invention in multiple labeling Monoclonal antibodies to human laminine and keratine (10 mg) were separately labeled with a 100-fold molar excess of the isothiocyanate derivatives of Eu chelates (82) and (83). The labeling was done in carbonate buffer, 50 mM, pH 9.8 by incubating overnight. The labeled antibodies were then purified from the free chelates by gel filtration through Sephadex G50 column (1.5×30 cm) eluting with Tris-HCl (50 mM, pH 7.75) containing 9 g of NaCl and 0.5 g of NaN₃ per liter. The bound chelate was quantified by measuring the $Eu^{3+}$ after cation dissociation with acid (Hemmilä et al., Anal. Biochem. 1984; 137: 335–43).

Cryostat sections of tissues were fixed in periodate-lysine-paraformaldehyde fixative. Immunofluorescence stainings were done according to standard procedures. The labeled antibodies were used in dilutions from 1:10 to 1:1000 and incubated with slides overnight at +4° C. The sections were dehydrated with ethanol and viewed uncovered with a fluorescence microscope (Laitz Dialux) equipped with an epi illumination filter block and mercury lamp. For excitations filters with bandpass from 340 nm to 380 nm were used and for emission a filter with narrow bandpass at 613 nm.

The fluorescence of the chelates was measured according to Kankare et al. (Eur. Pat. Appl. 86 85 0172.7).

The relative fluorescence of the chelates was calculated using the formula:

$$\frac{I_{che} \cdot c_{Eu} \cdot k_{Eu}}{I_{Eu} \cdot c_{che} \cdot k_{che}}$$

where $I_{che}$ and $I_{Eu}$ are pre-exponential terms for chelate and $Eu^{3+}$(aq) (used as reference), $c_{che}$ and $c_{Eu}$ are their concentrations, and $k_{che}$ and $k_{Eu}$ their decay constants, respectively.

For testing the solvent effect of the fluorescence of the chelates, the fluorescence was measured in borate buffer, pH 8.5 and in ethanol. The fluorescence properties of some chelates are presented in table 1.

TABLE 1

Fluorescence properties of some 6,6'-bis(N,N-bis(carboxymethyl)aminomethyl)-2,2'-bipyridines

| | $Eu^{3+}$ | | | | | | $Tb^{3+}$ | | | | | |
|---|---|---|---|---|---|---|---|---|---|---|---|---|
| | Borate buffer pH 8.5 | | | Ethanol | | | Borate buffer pH 8.5 | | | Ethanol | | |
| Substituents | 1 | 2 | 3 | 1 | 2 | 3 | 1 | 2 | 3 | 1 | 2 | 3 |
| Basic compound | 5.50 | 307 | 588 | | | | 6.83 | 307 | 1226 | | | |
| 4,4'-dimethyl | 5.61 | 310 | 592 | 5.59 | 310 | 649 | 7.07 | 308 | 1473 | 6.91 | 310 | 1144 |
| 4-nitro | 4.12 | 328 | 534 | 4.98 | 310 | 685 | 4.50 | 310 | 1411 | | | |
| | | | | 4.62 | 298 | 807 | | | | | | |
| 4,4'-dinitro | 4.14 | 338 | 535 | 3.45 | 336 | 375 | | | | | | |
| 4-amino | 4.42 | 290 | 581 | 4.77 | 292 | 722 | 6.18 | 294 | 1504 | 6.19 | 290 | 1665 |
| 4-ethoxy | 5.33 | 298 | 580 | 5.28 | 300 | 680 | 6.87 | 299 | 1605 | 6.79 | 300 | 1386 |
| 4,4'-diethoxy | 5.11 | 290 | 557 | 5.07 | 285 | 694 | 6.69 | 287 | 1501 | 6.66 | 280 | 1674 |
| 4-bromo | 5.36 | 315 | 569 | 5.23 | 315 | 658 | 6.68 | 310 | 1037 | 4.89 | 310 | 1247 + 80 |
| 4,4'-dibromo | 5.31 | 310 | 538 | 5.13 | 310 | 659 | 6.58 | 310 | 752 | 3.01 | 304 | 331 + 58 |
| 4,4'-bis(p-methoxyphenyl) | 5.57 | 325 | 562 | 5.69 | 325 | 678 | 6.40 | 325 | 326 | 4.99 | 328 | 718 + 76 |
| 4,4'-bis-(2-furyl) | 5.32 | 330 | 567 | 5.33 | 330 | 667 | 3.66 | 320 | 665 | 2.56 | 320 | 358 |
| 4,4'-distyryl | 2.95 | 315 | 571 | 2.74 | 315 | 499 | 4.19 | 313 | 903 | 3.15 | 313 | 299 |
| Basic compound-N,N'-dioxide | 4.72 | 280 | 741 + 196 | 4.94 | 280 | 1054 + 223 | 5.30 | 280 | 898 + 212 | 5.14 | 280 | 518 + 173 |
| 4-(phenylethynyl) | 5.36 | 330 | 565 | 5.38 | 330 | 801 | 4.88 | 319 | 81 | 3.63 | 318 | — |
| 4-(p-aminophenylethynyl) (59) | 4.18 | 317 | 577 | 4.35 | 317 | 718 | 4.37 | 312 | 545 | 3.80 | 298 | 50 |
| 4-(m-aminophenylethynyl) | 3.56 | 325 | 520 | 3.76 | 317 | 713 | 3.34 | 317 | 11 | 3.65 | 331 | 3 |
| 4-(p-isothiocyanatophenylethynyl) (60) | 5.30 | 342 | 572 | 5.23 | 344 | 582 | 4.54 | 309 | — | 3.79 | 322 | — |
| 4-(4-amino-3-(methoxycarbonyl-phenyl ethynyl) | 4.42 | 314 | 568 | 5.04 | 316 | 746 | 4.65 | 314 | 117 | 4.81 | 317 | 60 |
| 4-(4-hydroxy-3-(methoxycarbonyl)-phenyl-ethynyl) | 4.63 | 340 | 130 | 5.50 | 338 | 774 | 3.94 | 309 | — | 4.44 | 323 | 7 |
| Compound 80 | 5.21 | 298 | 565 | 5.25 | 300 | 640 | 6.64 | 298 | 1540 | 6.60 | 300 | 1380 |
| 6-(N-(carboxymethyl)-N-(1-(5-(p-amino-benzamido))-1-carboxypentyl)aminomethyl) -6'-N,N-bis(carboxymethyl)aminomethyl -2,2'-dipyridyl ketone | 3.70 | 272 | 1000 | 3.31 | 272 | 1110 | 4.91 | 272 | 1850 | 4.83 | 272 | 1890 |
| 5-bromo | 4.16 | 320 | 566 | 5.26 | 320 | 361 | 6.06 | 320 | 729 + 103 | 5.13 | 320 | 512 + 204 |
| 3,3'-dicarboxy | 4.90 | 283 | 575 | 4.87 | 290 | 691 | 3.79 | 280 | 1579 + 181 | 4.05 | 280 | 1007 + 123 |
| 4,4'-dicarboxy | 4.42 | 325 | 586 | 4.42 | 325 | 678 | 5.10 | 325 | 629+ | 3.82 | 325 | 613+ |
| 3,3'-bis(carbethoxy) | 4.31 | 275 | 556 | 4.32 | 275 | 642 | | | | | | |
| 3,3'-bis(benzoxy) | 5.36 | 292 | 543 | 3.52 | 296 | 247 | 4.39 | 290 | 629 + 103 | | | |
| 3,3'-dihydroxy | 3.91 | 340 | 382 | | | | | | | | | |
| 4,4'-diphenyl | 5.52 | 325 | 578 | 5.43 | 325 | 684 | 6.74 | 325 | 890 | 4.64 | 325 | 575 + 175 |

1 = Log (relative fluorescence)
2 = Excitation wavelength (nm)
3 = Decay time (μs)

SCHEME 1
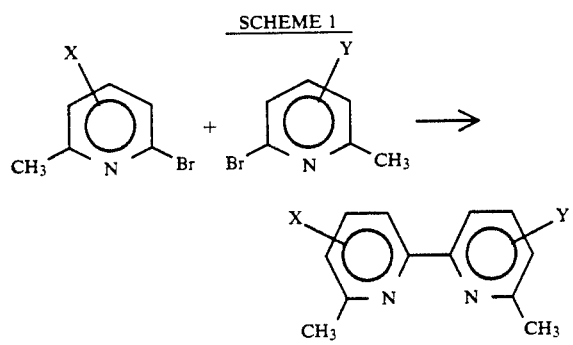
SCHEME 2
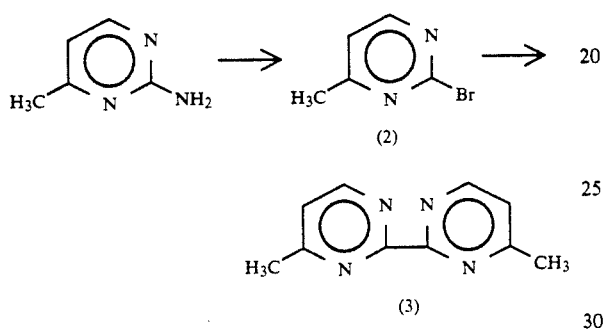
SCHEME 3
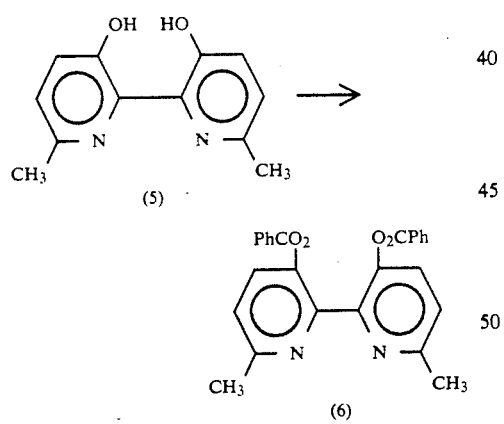
SCHEME 4
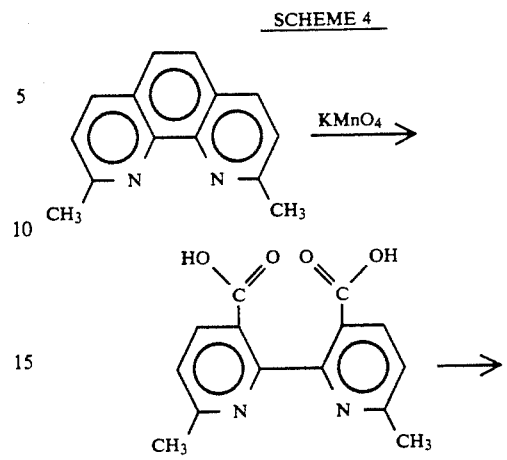
SCHEME 5
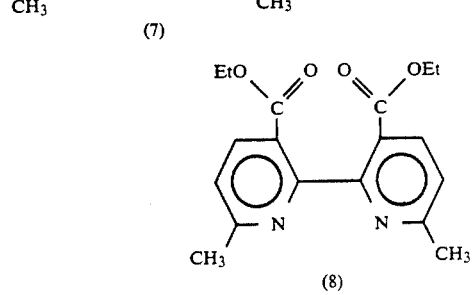
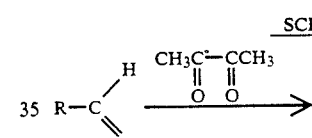
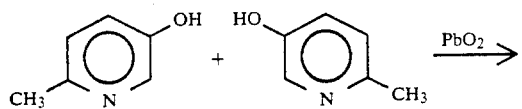
(10) R = Styryl
(67) R = Phenyl
SCHEME 6
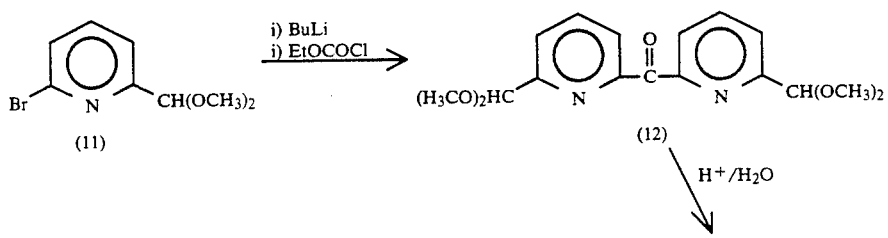

5,216,134
SCHEME 6 -continued
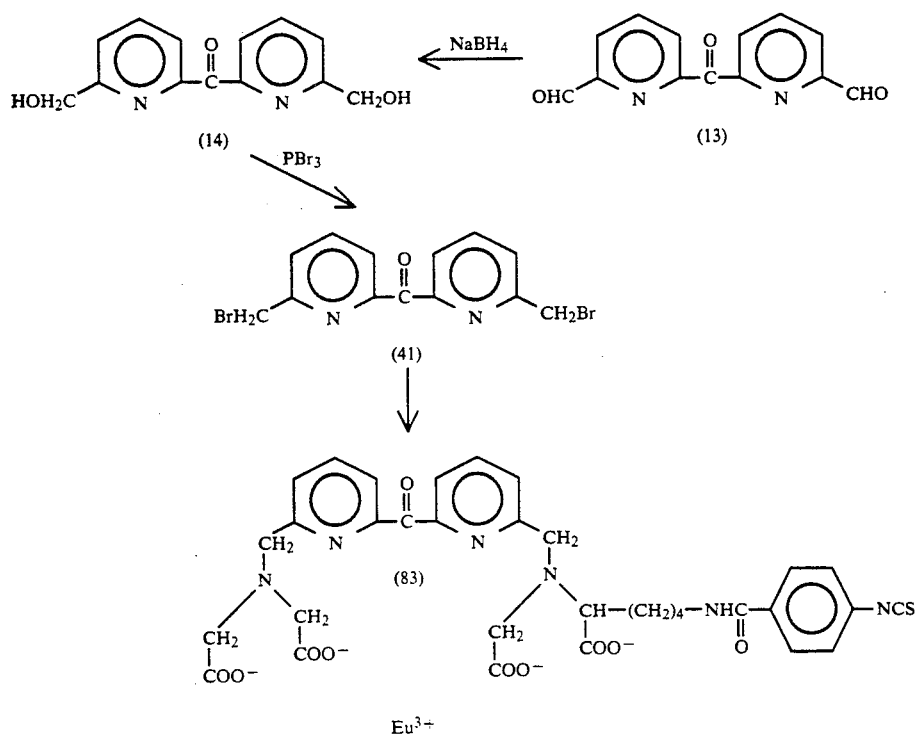
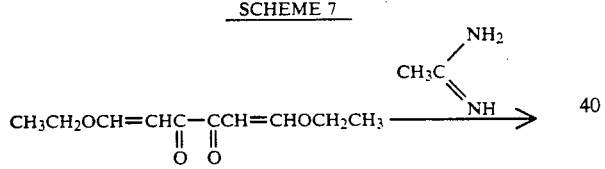
SCHEME 7
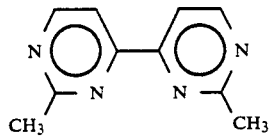
-continued SCHEME 7
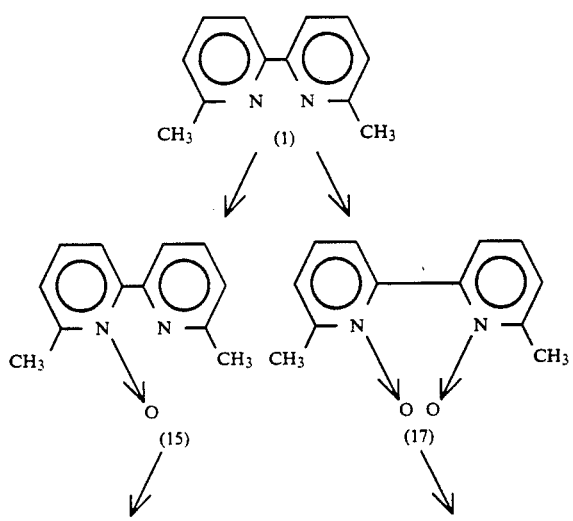
SCHEME 8

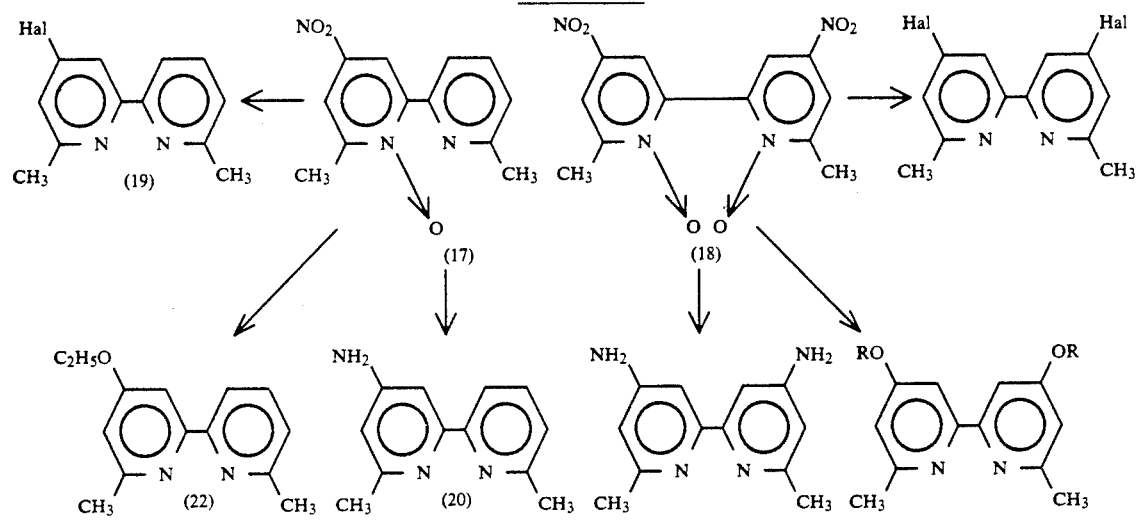
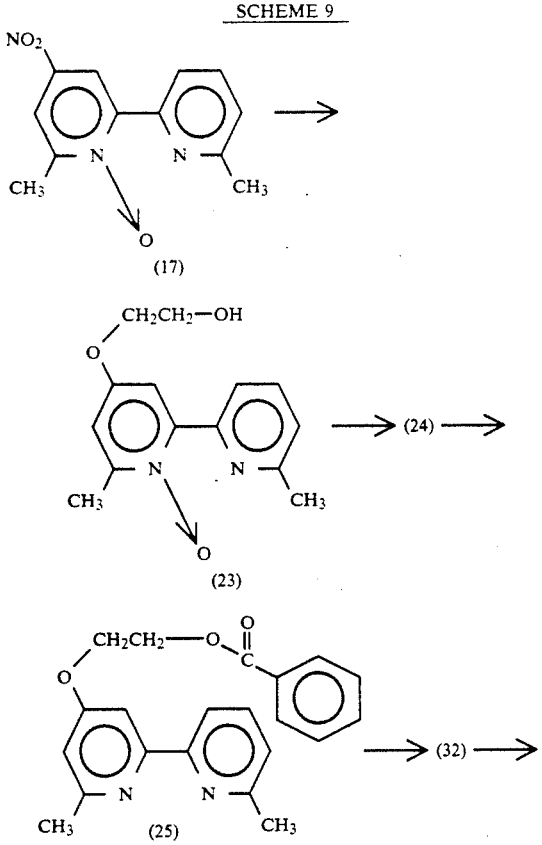
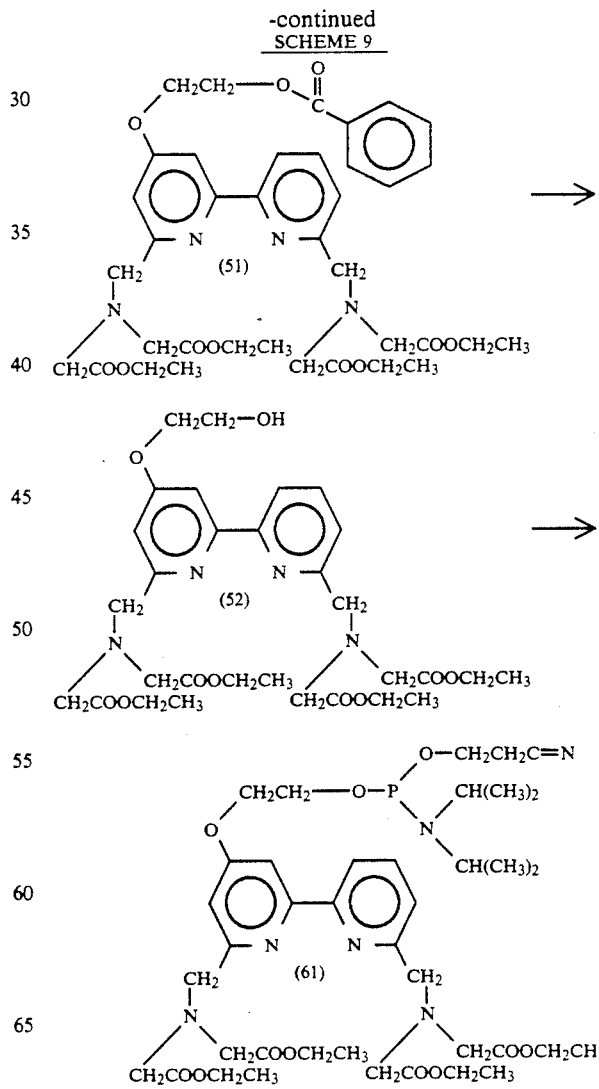

SCHEME 10
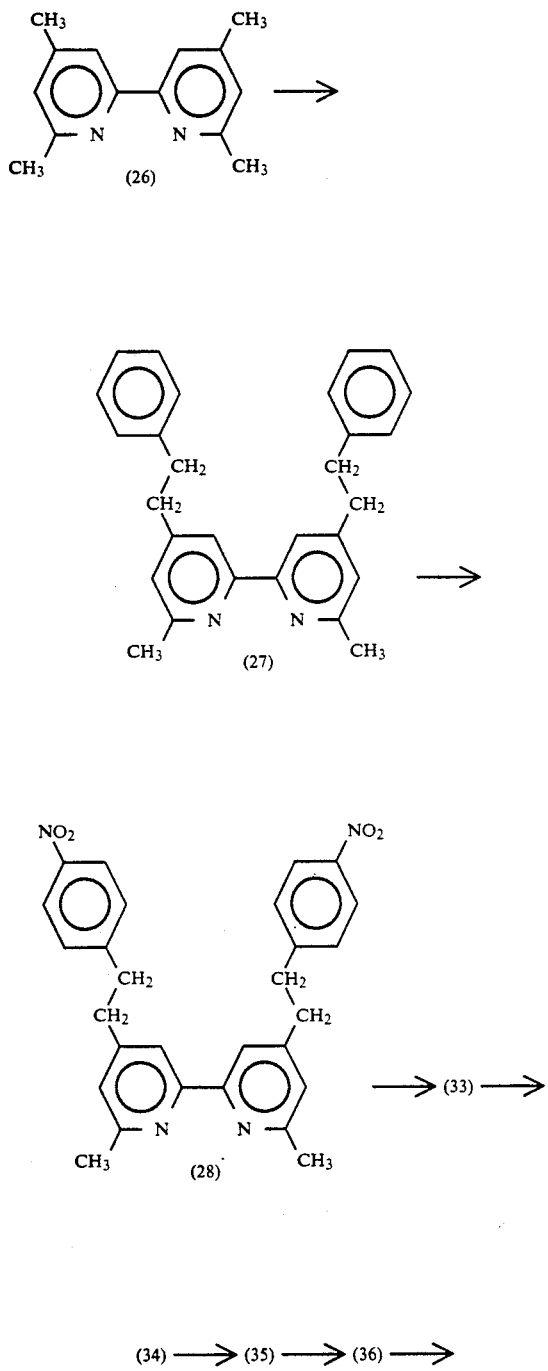
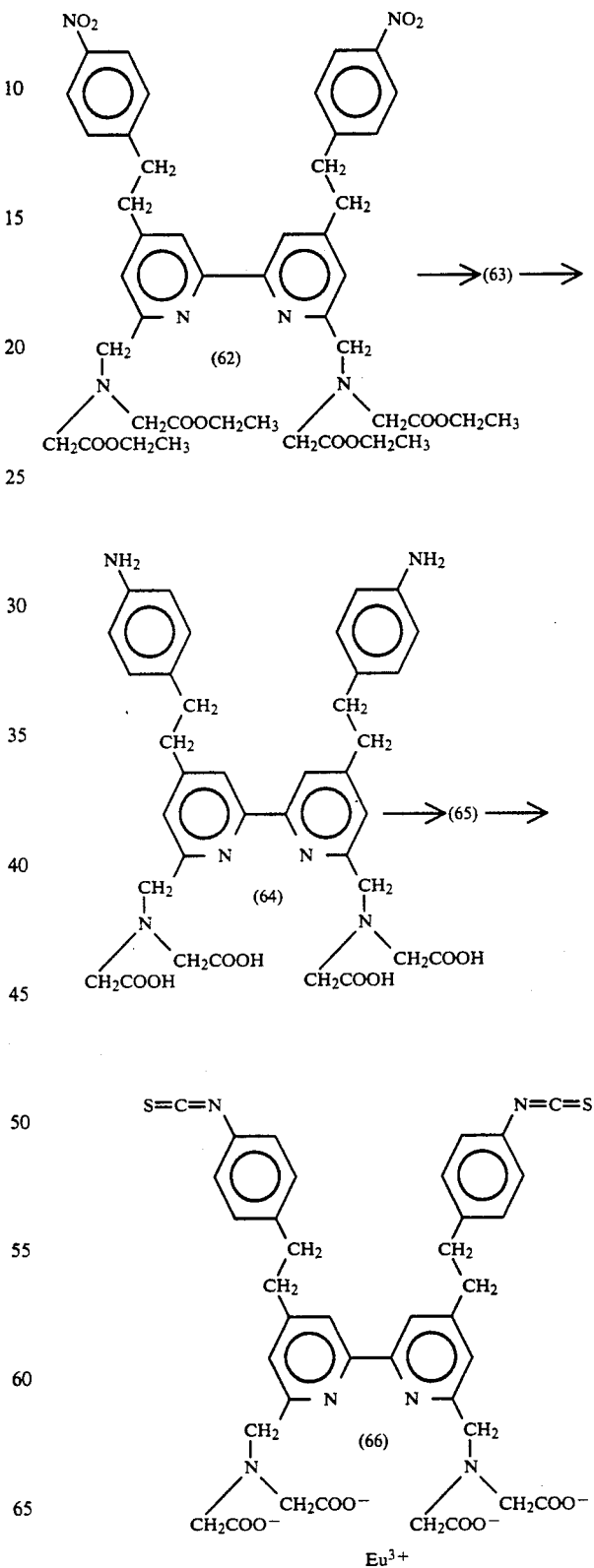

SCHEME 11
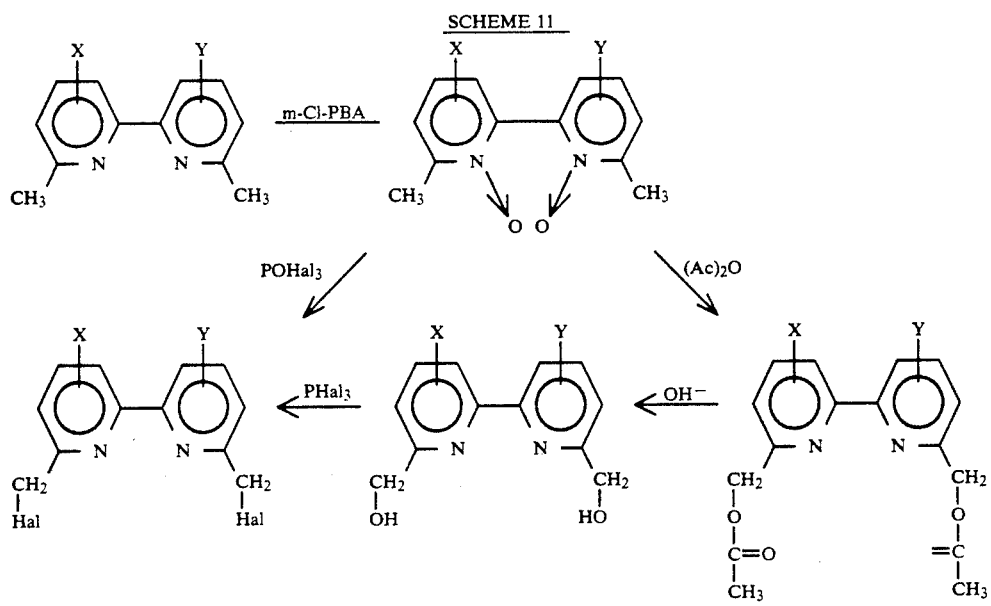
SCHEME 12
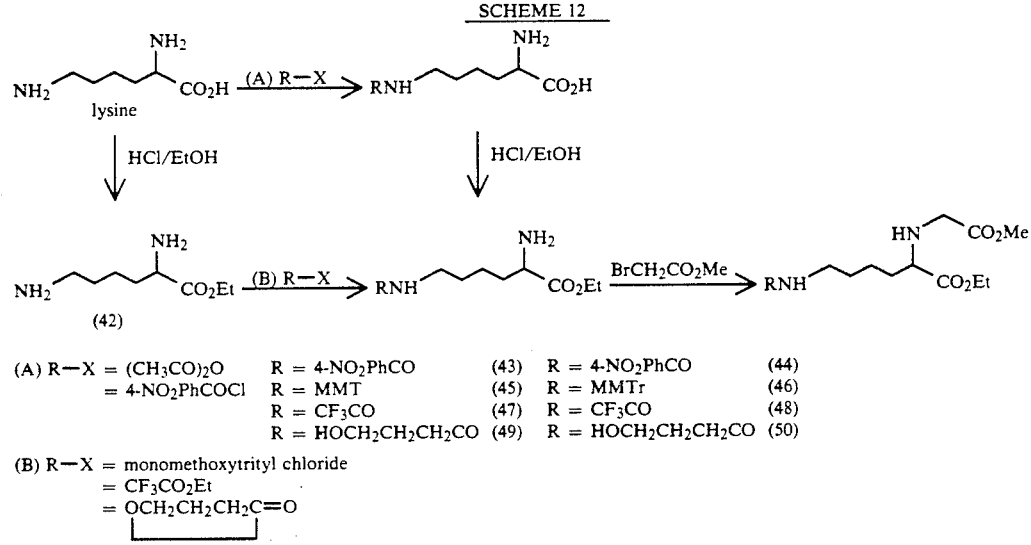
(A) R—X = (CH₃CO)₂O      R = 4-NO₂PhCO      (43)    R = 4-NO₂PhCO      (44)
      = 4-NO₂PhCOCl       R = MMT            (45)    R = MMTr           (46)
                          R = CF₃CO          (47)    R = CF₃CO          (48)
                          R = HOCH₂CH₂CH₂CO  (49)    R = HOCH₂CH₂CH₂CO  (50)
(B) R—X = monomethoxytrityl chloride
      = CF₃CO₂Et
      = OCH₂CH₂CH₂C=O

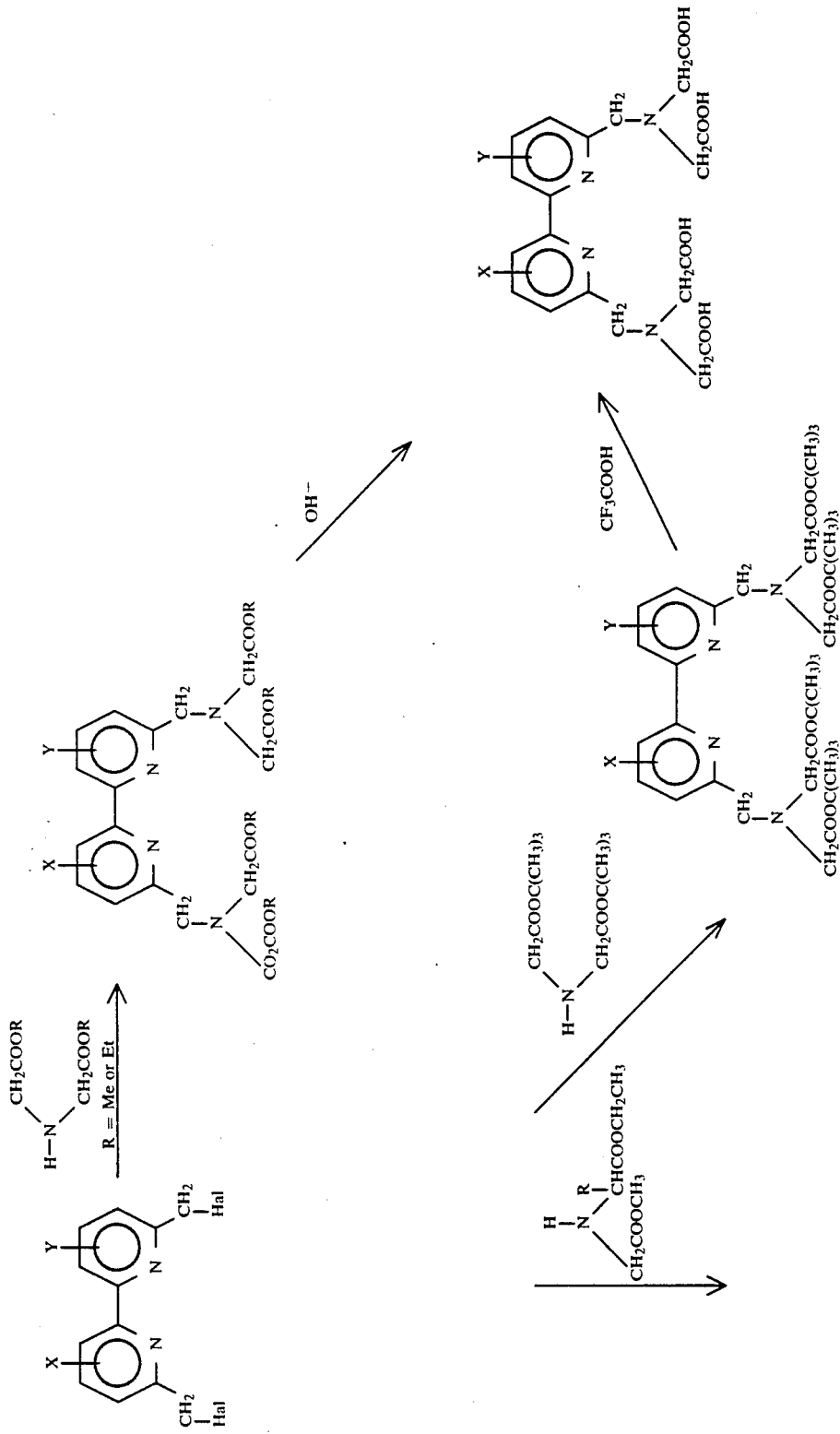

SCHEME 13 -continued
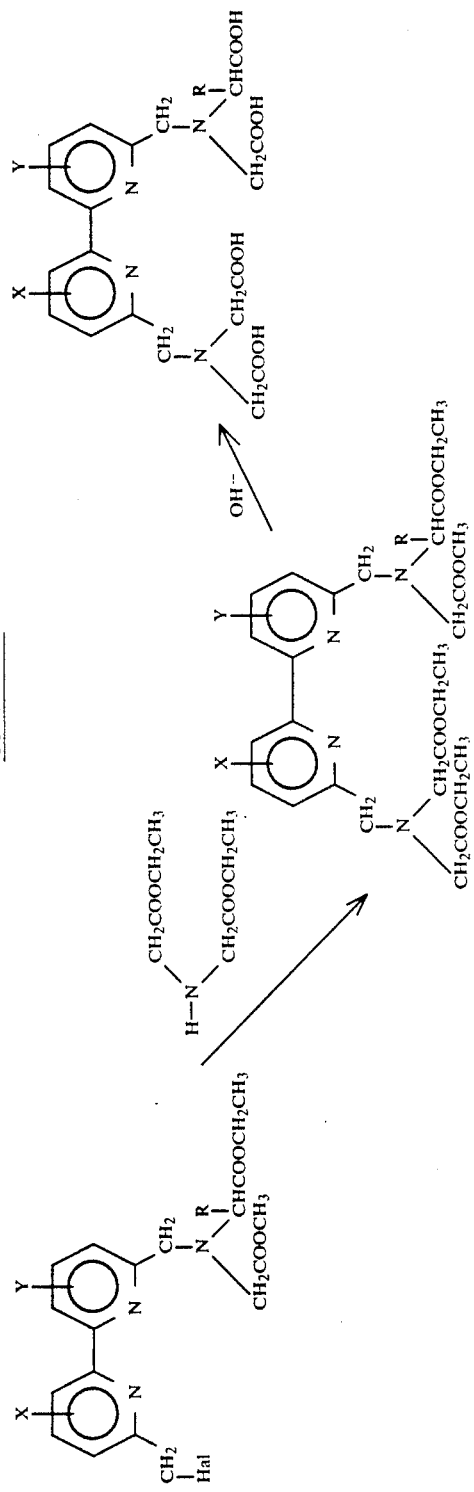

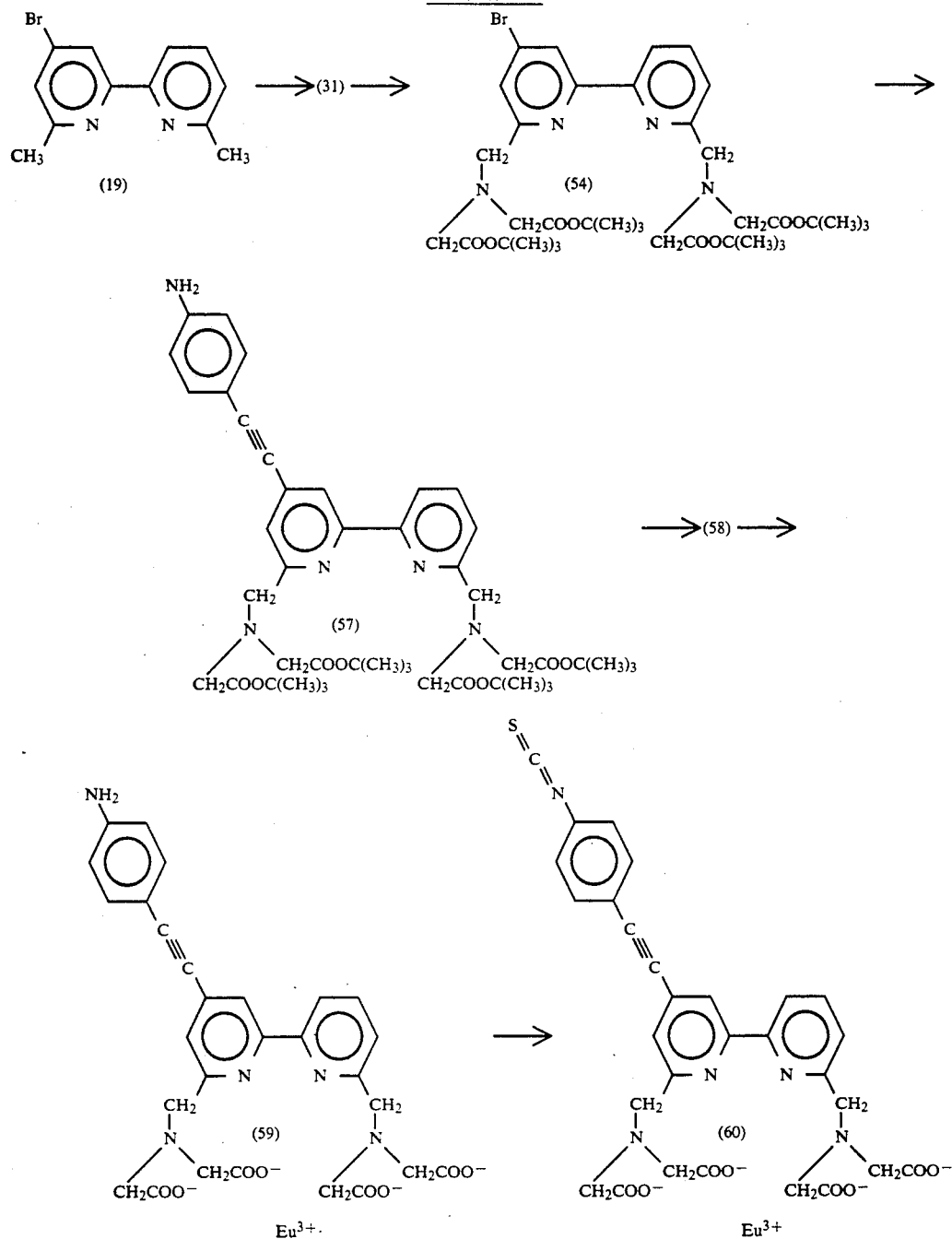

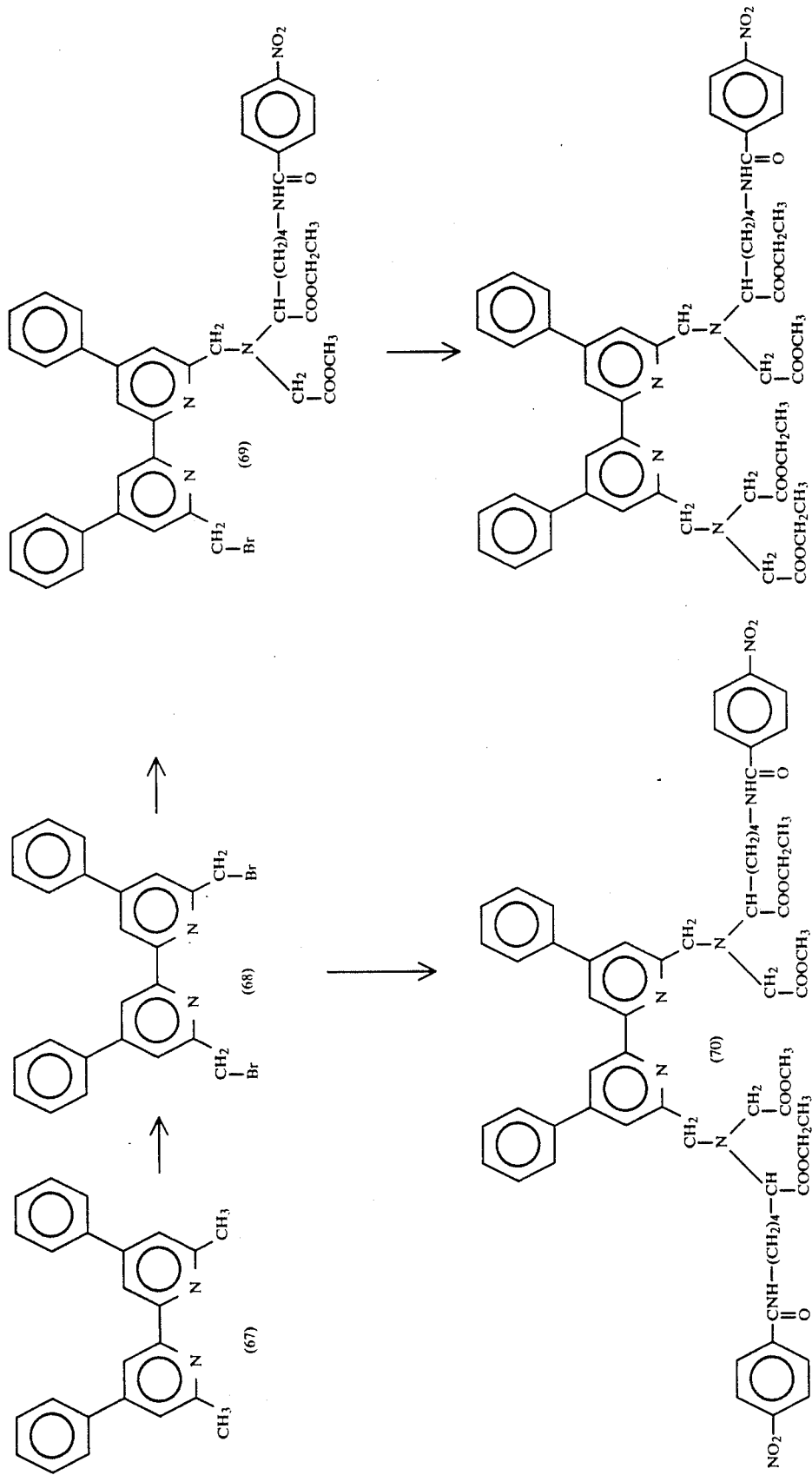

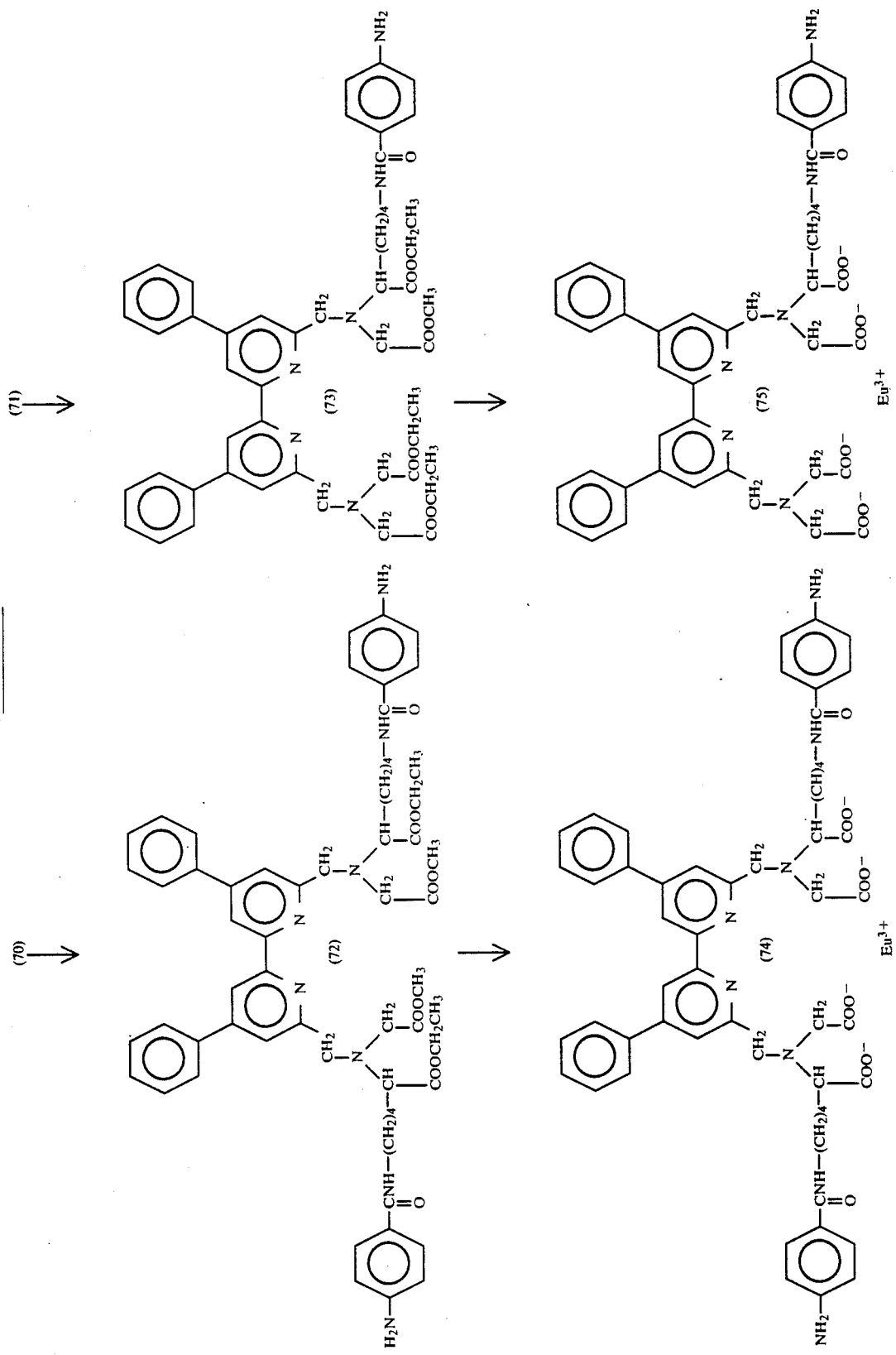

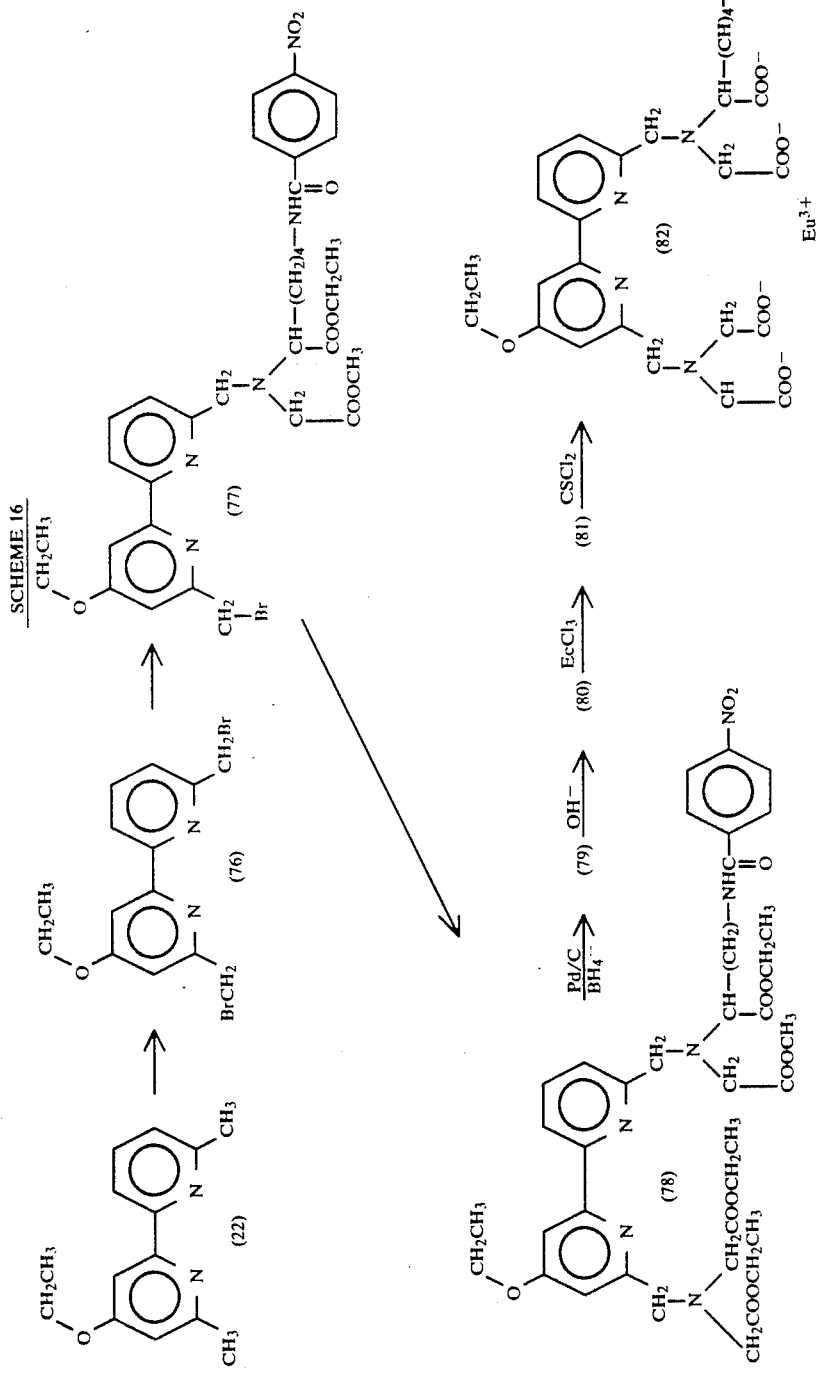

We claim:
1. A chelate formed between $Eu^{3+}$, $Tb^{3+}$, $Dy^{3+}$ and $Sm^{3+}$ and a compound having the formula

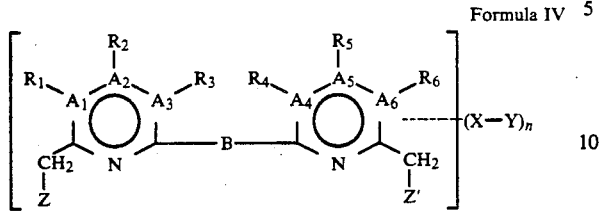

Formula IV

Parent Compound      Substituent where
- i $A_1$-$A_6$ are single atoms selected from the group consisting of a carbon atom and a nitrogen atom,
- ii n is 1 or 2,
- iii each of $R_1$-$R_6$ is nothing when the A to which it is attached is nitrogen; and for each A that is a carbon atom $R_1$-$R_6$ are selected from the group consisting of
  - (a) hydrogen, hydrocarbon group, cyano, halo, nitro and
  - (b) carboxy (—COOH), amido (—CONH$_2$), amino (—NH$_2$), hydroxy (—OH) and substituted forms of these four groups in which hydrogen is replaced with a hydrocarbon group according to (a) and for amino and hydroxy the hydrogens also have the possibility of being replaced with an acyl group (R—CO—) where R is a hydrocarbon group according to (a),
- iv Z and Z' represent identical or different chelating structures selected from the group consisting of N-biscarboxyethyl amino, N-biscarboxymethyl amino and the analogous phosphate (—N(—CH$_2$—O—PO$_3{}^{2-}$)$_2$ and phosphonate —N(—CH$_2$—PO$_3{}^{2-}$)$_2$, respectively),
- v B is selected from the group consisting of a direct link, —NH—, —CO— and —O—,
- vi —specifies that the group —X—Y is substituent replacing a hydrogen anywhere in the parent compound,
- vii X—Y represents an organic group in which X is stable in the sense that does not deteriorate when the compound is used and X—Y has no chelating heteroatom closer than four atoms from a chelating heteroatom in the parent compound of formula (IV), and Y is
  - (a) a functional group selected among isothiocyanato, bromoacetamido, iodoaceteamido, succinimido, pyridyldithio, mercapto, carboxyl and its active esters, hydroxyl, aldehyde, amino, diazonium, tosyl, mesytylyl, trexyl, phosphodiester or phosphotriester, or
  - (b) a residue of a biologically active molecule having the ability to participate in biospecific affinity reactions, and X consists of groups selected among —NR— (secondary or tertiary amine), —CONR— and —RNCO— (substituted amide), —S—S— (aliphatic disulfide), —S— (aliphatic thioether), —O— (ether), —COO— and —OOC— (ester), —N=N— (diaza) and pure hydrocarbon chain containing from 1 to 12 carbon atoms, in which groups R is an alkyl group having less than 5 carbon atoms, with the proviso that, when XY is attached to the heterocyclic rings of formula IV, X has a methylene group (—CH$_2$—).

2. The chelate of claim 1 wherein Z and Z' are identical.
3. The chelate of claim 2 wherein each of Z and Z' are N-biscarboxymethyl.
4. The chelate of claim 1 wherein n=1, and X—Y replaces one of $R_1$-$R_6$, while the A to which X—Y is bound is carbon.
5. The chelate of claim 1 wherein X—Y replaces a hydrogen in at least one of Z and Z'.
6. The chelate of claim 1 wherein Y is a residue of a residue of a biologically active molecule having the ability to participate in biospecific affinity reactions and selected from the group consisting of antigens, haptens and antibody active components and nucleic acids.
7. The chelate of claim 1 wherein Y is a functional group selected among isothiocyanato, bromoacetamido, iodoacetamido, succinimido, pyridyldithio, mercapto, carboxyl and its active esters, hydroxyl aldehyde, amino, diazonium, tosyl, mesytylyl, trxyl, phosphodiester or phosophotriester.
8. The chelate according to claim 1 wherein only one of $A_1$-$A_6$ is nitrogen.
9. The chelate according to claim 1 wherein only one of $A_1$-$A_3$ is nitrogen and only one of $A_4$-$A_6$ is nitrogen.
10. A chelate of 4-ethoxy-6-(N-(carboxymethyl)-N-(1-(5-p-isothiocyanatobenzamido))-1-carboxypentyl)aminomethyl)-6'-(N,N-bis(carboxymethyl)aminomethyl)-2-2'-bipyridine that is bound to an antibody via its p-isothiocyanato group wherein the chelated metal ion is selected from $Eu^{3+}$ and $Tb^{3+}$.
11. A chelate of 6-(N-(carboxymethyl)-N-(1-(5-p-isothiocyanatobenzamido))-1-carboxypentyl)aminomethyl)-6'-(N,N-bis(carboxymethyl)aminomethyl)-2-2'-dipyridyl ketone that is bound to an antibody via its p-isothiocyanato group wherein the chelated metal ion selected from $Eu^{3+}$ and $Tb^{3+}$.

* * * * *